United States Patent [19]

Szmuszkovicz

[11] Patent Number: 4,540,690

[45] Date of Patent: Sep. 10, 1985

[54] 2-(PHENYLMETHYLENE)CYCLOALKYLAMINES AND -AZETIDINES

[75] Inventor: Jacob Szmuszkovicz, Kalamazoo, Mich.

[73] Assignee: The Upjohn Company, Kalamazoo, Mich.

[21] Appl. No.: 408,333

[22] Filed: Aug. 16, 1982

Related U.S. Application Data

[63] Continuation-in-part of Ser. No. 347,123, Feb. 9, 1982, abandoned.

[51] Int. Cl.³ .................. C07D 205/04; C07D 405/08; A61K 31/36; A61K 31/395
[52] U.S. Cl. ..................... 514/210; 260/239 A; 549/362; 549/435
[58] Field of Search .............. 260/239 AR; 424/244, 424/278, 282; 549/362, 435

[56] References Cited

U.S. PATENT DOCUMENTS

| | | | |
|---|---|---|---|
| 3,458,523 | 7/1969 | Szmuszkovicz | 544/214 |
| 3,468,881 | 9/1969 | Szmuszkovicz | 260/239 B |
| 3,499,033 | 3/1970 | Szmuszkovicz | 546/236 X |
| 3,506,670 | 4/1970 | Szmuszkovicz | 260/239 B X |
| 3,558,599 | 1/1971 | Szmuszkovicz | 260/239 B |
| 3,595,867 | 7/1971 | Szmuszkovicz | 546/241 |
| 3,632,813 | 1/1972 | Szmuszkovicz | 546/237 |
| 3,651,232 | 3/1972 | Szmuszkovicz | 514/317 |
| 3,668,199 | 6/1972 | Szmuszkovicz | 260/239 B |
| 3,705,176 | 12/1972 | Szmuszkovicz | 548/578 |
| 4,098,904 | 7/1978 | Szmuszkovicz | 548/578 X |
| 4,145,435 | 3/1979 | Szmuszkovicz | 548/578 X |
| 4,242,261 | 12/1980 | Cale, Jr. | 260/239 A |
| 4,260,606 | 4/1981 | Cale, Jr. et al. | 260/239 A X |

OTHER PUBLICATIONS

*J. Am. Chem. Soc.*, (JACS), 82 (1960), pp. 2389-2393, R. D. Campbell et al., "β-Diketones. I.Synthesis and Reactions of Some 2-Benzoylcyclanones".

*JACS*, 82 (1960), pp. 5426-5434, R. D. Campbell et al., "β-Diketones.II.Ultraviolet . . . 2-Aroylcyclohexanones".

*JACS*, 84 (1962), pp. 2614-2620, H. O. House et al., "Synthesis . . . 8–Methylhexahydrofluorenone".

*J. of Org. Chem.*, 32 (1967), pp. 3300-3313, J. Szmuszkovicz et al., "Synthesis . . . 2–Amino–α–Phenylcyclohexanemethanol Series".

*JACS*, 90 (1968), pp. 509-510, J. E. Blackwood et al., "Unambiguous Specification of Stereoisomerism about a Double Bond".

*J. Med. Chem.*, 12 (1969), L. L. Skaletzky et al., "The Relationship . . . Diuretic Agents.II".

*J. Org. Chem.*, 36 (1971), B. V. Cheney, "A Nuclear . . . Cyclohexanemthanol".

*Primary Examiner*—Donald G. Daus
*Assistant Examiner*—William A. Teoli, Jr.
*Attorney, Agent, or Firm*—John T. Reynolds

[57] ABSTRACT 2-(Phenylmethylene)cycloalkylamines and -azetidines of the formula

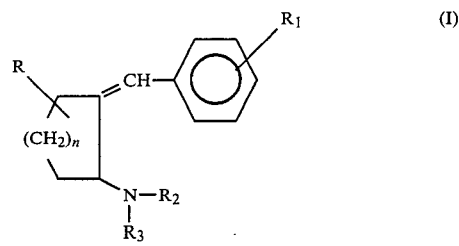

and acid addition salts thereof, e.g., 1-[2-(phenylmethylene)cyclohexyl]azetidine, and related compounds, which have analgesic, antidepressant and mixed analgesic/antidepressant central nervous system (CNS) activities, and which are useful in treating pain and/or depression in mammals including humans. The invention provides processes for preparing the compounds as well as compositions containing the compounds and methods for using the compounds as analgesic and/or antidepressant drugs for humans and valuable mammalian animals.

51 Claims, No Drawings

2-(PHENYLMETHYLENE)CYCLOALKYLAMINES AND -AZETIDINES

CROSS REFERENCE

This is a continuation-in-part of application Ser. No. 06/347,123, filed Feb. 9, 1982 now abandoned.

INTRODUCTION

This invention relates to some new 2-(phenylmethylene)cycloalkylamine and -azetidine compounds which have analgesic activity, antidepressant activity, or mixed analgesic/antidepressant central nervous system (CNS) activities, which activities makes the compounds useful as analgesic and/or antidepressant drugs for treating pain and/or depression in mammalian animals including humans. This invention also discloses processes for preparing these compounds, compositions containing such compounds and methods for using such compounds as analgesics and/or as antidepressant drugs.

BACKGROUND OF THE INVENTION

Szmuszkovicz U.S. Pat. No. 3,468,881 discloses some allylic amines, having anti-depressive action of the formula

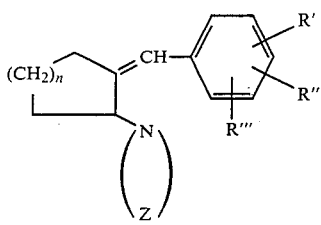

wherein the group

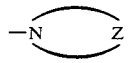

is selected from the group consisting of pyrrolidino, piperidino, morpholino, 4-methylpiperazino and hexahydro-1H-azepin-1-yl(hexamethyleneimino), and wherein R', R" and R''' are hydrogen or $C_1$ to $C_4$-alkyloxy. However, such compounds are less potent as analgesic and antidepressant compounds.

Szmuszkovicz U.S. Pat. No. 3,506,670 discloses some 1,3-amino-alcohols of the formula

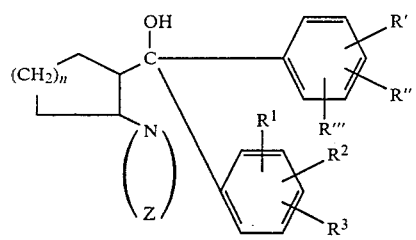

wherein —N Z is a heterocyclic amino radical containing from five to ten nuclear atoms, inclusive, e.g., pyrrolidino, 2-methylpyrrolidino, 2-ethylpyrrolidino, 2,2-dimethylpyrrolidino, 3,4-dimethylpyrrolidino, 2-isopropylpyrrolidino, 2-sec.-butylpyrrolidino, and like alkylpyrrolidino groups, morpholino, 2-ethylmorpholino, 2-ethyl-5-methylmorpholino, 3,3-dimethylmorpholino, thiamorpholino, 3-methylthiamorpholino, 2,3,6-trimethylthiamorpholino, 4-methylpiperazino, 4-butylpiperazino, piperidino, 2-methylpiperidino, 3-methylpiperidino, 4-methylpiperidino, 4-propylpiperidino, 2-propylpiperidino, 4-isopropylpiperidino, and like alkylpiperidino groups, hexamethyleneimino, 2-methylhexamethyleneimino, 3,6-dimethylhexamethyleneimino, homomorpholino, 1,2,3,4-tetrahydroquinolyl, heptamethyleneimino, octamethyleneimino, 3-azabicyclo[3.2.2]nonan-3-yl, 2-azabicyclo[2.2.2]octan-2-yl, and the like, and R', R", R''', R, $R^2$ and $R^3$ are defined variously as hydrogen, halogen, lower alkyl, lower alkoxy or trifluoromethyl, which are disclosed as being useful as oral and parenteral diuretics in mammals. But such patent does not teach the compounds claimed herein or the use as analgesics, claimed herein.

Szmuszkovicz U.S. Pat. No. 3,705,176 discloses some 1,3-aminoalcohol compounds of the formula

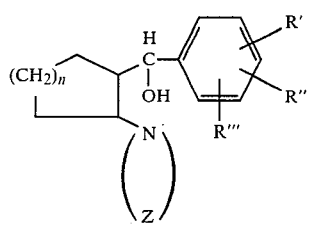

as oral antidiabetic agents. This patent defines

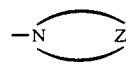

as a heterocyclic amino radical similar to the definitions above for defining the

in the U.S. Pat. No. 3,506,670 patent, but does not include any azetidine compounds therein.

Pain is a major health problem since it is a concomitant of myriads of illnesses. It is especially troublesome in chronic illness because: (1) many strong analgesics lose their effectiveness when given for long periods of time, and (2) continued suffering plus the resultant restrictions on activity often lead to a state of depression, which further inhibits activity and the enjoyment of life. There is a need for a good analgesic which does not cause tolerance during chronic use. Associated antidepressant activity might also prevent or alleviate the depressive element in chronic illness.

The available strong analgesics, narcotics, are also limited by government restrictions, because of the potential for abuse, and by their side effects, which can range from nuisance to life-threatening. Among these are respiratory depression, physical dependence, hallucinations, constipation, urinary retention and precipitation of opiate withdrawal. These qualities, taken with the decreasing effectiveness of chronically administered opiates, mean that there is inadequate treatment for patients with substantial chronic pain.

A number of patents have issued recently describing various N-(2-aminocycloaliphatic)benzeneacetamide derivative compounds (e.g. U.S. Pat. No. 4,145,435) and N-(2-aminocycloaliphatic)benzamide derivative compounds (e.g., U.S. Pat. No. 4,098,904) as analgesic compounds. These above patents have included within their description definitions of the 2-amino groups thereof as including azetidinyl rings as the amino group. However, those compounds are 2-amino-cycloaliphaticamide compounds (bearing 2 nitrogens on positions 1 and 2 of the cycloaliphatic ring) and function somewhat differently than the new compounds described and claimed herein.

OBJECTS OF THE INVENTION

It is an object of this invention to provide some new safe and effective analgesic compounds useful for treating mild and moderate pain in humans and valuable, warm-blooded animals.

It is a further object of this invention to provide some new centrally acting analgesic compounds which also possess some antidepressant-like properties and which do not induce tolerance development giving these compounds special usefulness in chronic pain which is often accompanied by depressive elements.

It is another object of this invention to provide some new centrally acting analgesic compounds which are not opiates and do not have troublesome narcotic characteristics such as opiate physical dependence, tolerance, respiratory depression, constipation, antidiuresis, psychotomimetic dysphoria or precipitation of opiate withdrawal, and which will be useful for treating chronic pain conditions over extended periods of time.

It is also an object and purpose of this invention to provide some new oral analgesic compounds which also have antidepressant properties, and which are free of opiate side effects and free of tolerance development.

It is another object of this invention to provide 2-(phenylmethylene)cycloalkylamine and -azetidine derivative compounds which have more potent antidepressant properties than analgesic properties, at least in terms of ED$_{50}$ potency numbers.

It is another object of this invention to provide compositions of these new 2-(phenylmethylene)cycloalkylamine and -azetidine compounds or salts thereof, which compositions are useful in pharmaceutical dosage quantities as analgesic and/or antidepressant drugs.

It is also an object of this invention to provide a method for treating human and valuable animal patients suffering pain and/or depression by administering to said patient an analgesic effective amount or an antidepressant effective amount of one of these 2-(phenylmethylene)cycloalkylamine, or -azetidine compounds or a pharmaceutically acceptable salt thereof.

Other objects and advantages of this invention will become apparent to persons skilled in the art from reading the remainder of the specification.

SUMMARY OF THE INVENTION

Briefly this invention provides a group of new 2-(phenylmethylene)cycloalkylamine and -azetidine compounds and salts, thereof as new compounds which have been found to have useful potencies of analgesic properties and/or antidepressant properties, or combined analgesic/antidepressant properties in standard laboratory animal tests.

A lead compound in this group, the E-isomer of (∼)-1-[2-(phenylmethylene)cyclohexyl]azetidine, and its pharmaceutically acceptable salts, e.g., its succinate salt, has been found to be a non-opiate, safe and effective analgesic drug having desirable antidepressant properties.

The main process for preparing the 1-[2-(phenylmethylene)cycloalkyl]amine or -azetidine compounds involves three or four steps starting with the selected cycloalkanone (1) to the cycloalk-1-enylmorpholine, (2) to the 2-(phenylmethylene)cycloalkanone, (3) to the 2-(phenylmethylene)cycloalkylamine, and (4) optionally, to the 1-[2-(phenylmethylene)cycloalkyl]azetidine and to the respective salts for isolation, purification and/or pharmaceutical composition preparation.

The compositions of this invention comprise the selected 1-[2-(phenylmethylene)cycloalkyl]amine or -azetidine compound, or a pharmaceutically acceptable acid addition salt thereof mixed with a diluent useful for making pharmaceutical dosage unit forms of the selected active 1-[2-(phenylmethylene)cycloalkyl]amine or -azetidine ingredient.

The method of use of this invention comprises administering to a human or valuable animal suffering pain and/or depression a safe, but analgesically and/or antidepressant effective amount of the selected 1-[2-(phenylmethylene)cycloalkyl]amine or -azetidine, or a pharmaceutically acceptable salt thereof.

DETAILED DESCRIPTION OF THE INVENTION

More specifically, this invention provides new, useful drug compounds of the formula (I)

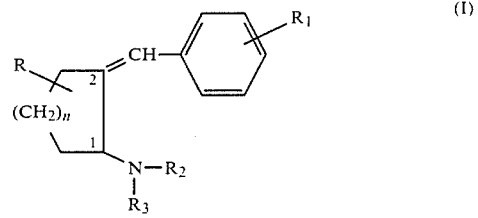

wherein
n is 1, 2, 3, or 4 so that the resulting cycloalkyl ring is cyclopentyl, cyclohexyl, cycloheptyl or cyclooctyl;

R is hydrogen, $C_1$ to $C_3$-alkyl; or when n is 2, R can be an —O—$(CH_2)_m$—O— group where m is 2 to 3 bonded to carbon atom number 4 of the cycloaliphatic ring so that the compound is a (1,4-dioxaspiro[4.5]-dec-8-yl)amine compound;

$R_1$ represents hydrogen or at least one (preferably no more than two) substituent(s) on the phenyl ring selected from the group consisting of a halogen having an atomic number of from 9 to 35 (fluorine, chlorine or bromine), $C_1$ to $C_4$-alkyl,
trifluoromethyl,
hydroxy,
carboxyl, and sodium and potassium salts thereof,
$C_1$ to $C_2$-alkyloxy;
$C_1$ to $C_2$-alkyloxycarbonyl (C(O)O-$C_1$-$C_2$-alkyl),
$C_2$ to $C_5$-alkanoyloxy (—OC(O)-$C_1$-$C_4$-alkyl), hydroxymethyl,
($C_1$ to $C_2$-alkanoyl)oxymethyl (—$CH_2$O—$C_1$-$C_2$-alkanoyl),
O$(CH_2)_r$—O— bonded to the 3- and 4-ring carbons, where r is 1 or 2, ($C_1$ to $C_3$-alkyl)oxymethyl ($C_1$ to $C_3$—alkyl—O—$CH_2$), ($C_1$ to $C_2$—alkyl)oxycarbonylmethyl ($C_1$ to $C_2$-alkyl—O—C(O)—$CH_2$—), —CH($R_{10}$)-C(O)-O$R_{11}$ wherein $R_{10}$ is hydrogen or $C_1$ to $C_3$-alkyl and $R_{11}$ is hydrogen or $C_1$ to $C_3$-alkyl, phenyl, phenoxy, benzyloxy, benzoyloxy, phenyl-$C_1$ to $C_3$-straight or branched alkyl, phenylethenyl, phenoxymethyl, and said phenoxy, phenyl, benzyloxy, benzoyloxy, phenyl-$C_1$ to $C_3$-alkyl, phenylethenyl and phenoxymethyl groups substituted on the phenyl ring carbon atoms thereof with one or two halogens as defined above, trifluoromethyl $C_1$ to $C_2$-alkyl, $C_1$ to $C_2$-alkyloxy, and hydroxy;

$R_2$ and $R_3$ are each hydrogen or $C_1$ to $C_3$-alkyl, or $R_2$ is hydrogen or $C_1$ to $C_3$-alkyl when $R_3$ is $C_1$ to $C_4$-alkyl, cyclopropyl, cyclobutyl, 2-furylmethyl, 3-furylmethyl, benzyl, allyl, or 2-phenyl-1-propen-3-yl, or $R_2$ and $R_3$ are taken together with the nitrogen to which they are bonded to complete an aziridine ring or an azetidine ring of the formula

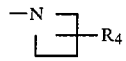

wherein $R_4$ denotes hydrogen, $C_1$ to $C_2$-alkyl, 3-hydroxy, 3-($C_1$ to $C_2$-alkyloxy) or 3-($C_1$ to $C_2$-alkanoyloxy);

and the acid addition salts of such compounds.

In the above formula I compounds, the term "$C_1$ to $C_2$-alkyl" means the methyl and ethyl groups. The term "$C_1$ to $C_3$-alkyl" further includes n-propyl and isopropyl groups. The term $C_1$ to $C_4$-alkyl further includes the butyl group in its various isomeric forms. The term "$C_1$ to $C_2$-alkyloxy" means methyloxy and ethyloxy. The term "$C_1$ to $C_2$-alkyloxycarbonyl" means methoxycarbonyl ($CH_3OC(O)$—) or ethyloxycarbonyl $C_2H_5$—OC(O)—. The term "$C_2$ to $C_5$-alkanoyloxy" means acetyloxy, propionyloxy, butanoyloxy or pentanoyloxy, e.g., $CH_3COO$— is acetyloxy.

Examples of acid addition salts of these compounds include the hydrohalide salts such as the hydrochloride, hydrobromide, hydrofluoride and hydroiodide, the sulfate and bisulfate, various phosphorus acid salts, the methanesulfonate, the p-toluenesulfonate, the benzoate, the acetate, and other alkanoic acid salts, as well as the salts of various dicarboxylic and tricarboxylic acids such as maleic, succinic, fumaric, malic, oxalic, itaconic acids, and the like. Some of these acids, e.g., oxalic acid, may be preferred for extracting the active amine or azetidine derivative from its reaction mixture, while other acids, e.g., succinic, maleic or p-toluenesulfonic may be preferred when the resulting amine or azetidine salt is to be formulated into pharmaceutically useful form. Also, the formula I compound and its acid addition salt in their crystalline state may sometimes be isolated as solvates, i.e., with a discrete quantity of water or other solvent such as ethyl acetate, ethanol, and the like, associated physically and thus removable without effective alteration of the active chemical drug entity per se.

A number of these salts were prepared of the lead compound (±)-(E)-1-[2-(phenylmethylene)cyclohexyl]azetidine with the aim of finding a salt which: (1) has acceptable water solubility; (2) is nonhygroscopic; (3) does not form hydrates under the conditions of synthesis; and (4) gives reproducible elemental analysis. With these as criteria, the succinate salt was chosen for further development.

The compounds of the formula I can have either of two configurations about the double bond as depicted in formulas Ia and Ib. These two configurations are termed (E) and (Z) as described by J. E. Blackwood et al., in the *Journal of the American Chemical Society*, Volume 90, pages 509 and 510 (1968). Briefly in general when a compound of this invention is represented by the formula I above, the (E)-isomer (formula Ia) is that in which the hydrogen atom on the double bond is explicitly shown below the carbon atom to which it is attached and the $R_1$-substituted phenyl ring is concurrently shown above the carbon atom to which it is attached. If the hydrogen atom n the double bond and the $R_1$-substituted phenyl ring of the (E)-isomer are interchanged, the resulting isomer is the (Z)-isomer (formula Ib). When the double bond involving carbon atom number two in the formula I above is formed or when such double bond is formed in an intermediate compound, a mixture of E and Z isomers generally results, with the E isomer usually predominating. This E-Z isomer mixture of formula I compounds can be used as such to practice this invention or the E and Z isomers can be separated, for example by chromatography or as exemplified below by a derivatization-separation-regeneration sequence, and the substantially pure E and Z isomers can be used to practice this invention.

The cycloalkyl ring carbon atom bearing the amino nitrogen is asymmetrically substituted for all of the formula I compounds. When R is $C_1$ to $C_3$-alkyl, the cycloaliphatic ring carbon atom to which R is bonded is asymmetrically substituted. When $R_2$ and $R_3$ are taken together with the nitrogen to which they are bonded to complete an azetidine ring substituted by a nonhydrogen $R_4$ substituent, the ring carbon atom bearing $R_4$ is asymmetrically substituted. Thus both the E- and Z-isomers of the formula I compounds of this invention have at least one and possibly two or three asymmetrically substituted carbon atoms. This invention includes all of the various isomers resulting from the presence of such asymmetrically substituted carbon atoms in E- and Z-isomers. Thus this invention includes the formula Ia and formula Ib amine and azetidine compounds as the various possible racemates, mixtures of enantiomers, mixtures of diastereomers and the substantially pure individual enantiomers and diastereomers. As a practical matter, however, it is not vitally necessary to separate the compounds with the pure structural configurations of the compounds of this invention to have active, useful drug product compounds.

If desired the formula I compounds of this invention can be resolved into their respective d- and l-optical isomers by methods known in the art. In this case, the optical resolution can be done by at least two different routes. The resolving agents by either route are any of the known resolving agents such as optically active dibenzoyltartaric acid, camphorsulfonic acid, bis-o-toluoyltartaric acid, tartaric acid, and diacetyl tartaric acid which are commercially available and which are commonly used for resolution of amines (bases), as for example in *Organic Synthesis*, Coll. Vol. V., p. 932

(1973), resolution of R-(+) and S-(−)-α-phenylethylamine with (−)-tartaric acid.

By one preferred method for resolving the compounds of this invention, for example, one of the formula I azetidine or other amine compounds can be converted into its optically active diastereomeric salts by reaction with an optically active acid—examples mentioned above—in a manner standard in the isomer resolution art. These diastereomeric salts can then be separated by conventional means such as differential crstallization. Diastereomeric salts have different crystallization properties, which are taken advantage of in this separation. On neutralization of each diastereomeric salt with aqueous base the corresponding optically active enantiomers of the formula I azetidine or other amine compound can be obtained, each of which can subsequently and separately be converted as hereinafter described in the examples to the desired acid addition salt.

Alternatively an amine-containing precursor to a formula I compound can first be resolved as above and then converted to an optically active form of a formula I compound.

In one method to prepare optical isomers of formula I compounds bearing nonhydrogen $R_4$ or $C_1$ to $C_3$-alkyl R groups, the appropriate precursor compounds bearing such groups can be resolved, and the resulting separated optical isomers can be reacted as herein described to produce optically active formula I compounds of this invention.

Pharmacologically speaking, and considering the lead compound, the E-isomer of (±)-1-[2-(phenylmethylene)cyclohexyl]azetidine appears to be somewhat more potent than the Z-isomer of the same compound. With regard to the E-isomer of this lead compound, each of the substantially pure (+)- and (−)-enantiomers when tested separately has shown antidepressant like drug effects in animal tests, with the (−)-isomer being somewhat more potent in this regard. In analgesic testing in both mice (HCl writhing) and rats (hot plate test) analgesic activity has only been demonstrated for the (−)-enantiomer. However, the potency of the (−)-isomer of this lead compound in these tests is not greater than that of the racemic mixture of this compound. Thus both enantiomers of this compound contribute to the observed analgesic and antidepressant test results obtained with the racemic mixture of this compound, and it is preferred to use the racemate of (E)-1-[2-(phenylmethylene)cyclohexyl]azetidine to obtain the analgesic and antidepressant effects of this invention. We believe, however, that both of the E- and Z-isomers of the various formula I compounds of this invention have various useful combinations of analgesic and antidepressant properties, ranging from substantially pure analgesic through mixed analgesic/antidepressant to substantially pure antidepressant properties.

One preferred group of compounds of this invention are those of formula II wherein each of $R_5$ and $R_6$ is selected from the group consisting of hydrogen, halogen having an atomic number of from 9 to 35, $C_1$ to $C_4$-alkyl, trifluoromethyl, hydroxy, carboxyl and sodium and potassium salts thereof, $C_1$ to $C_2$-alkyloxy, ($C_1$ to $C_2$-alkyloxy)carbonyl, $C_2$ to $C_5$-alkanoyloxy, hydroxymethyl, ($C_1$ to $C_2$-alkanoyloxy)methyl, —O—(CH$_2$)$_r$—O— bonded to the 3- and 4-ring carbons where r is 1 or 2, ($C_1$ to $C_2$-alkyloxy)methyl, 13 CH($R_{10}$)—C(O)—O$R_{11}$ wherein $R_{10}$ is hydrogen or $C_1$ to $C_3$-alkyl and $R_{11}$ is hydrogen or $C_1$ to $C_3$-alkyl, phenyl, phenoxy, benzyloxy, benzoyloxy, phenyl-$C_1$ to $C_3$-alkyl, phenylethenyl, phenoxymethyl and said phenyl ring containing groups substituted on phenyl ring carbons thereof with one or two substituents selected from the group consisting of halogen as defined above, trifluoromethyl, $C_1$ to $C_2$-alkyl, $C_1$ to $C_2$-alkyloxy and hydroxy, or a pharmaceutically acceptable salt thereof.

Examples of such compounds include:
1-[2-(phenylmethylene)cyclohexyl]azetidine,
1-[2-(4-bromophenylmethylene)cyclohexyl]azetidine,
1-[2-(3,4-difluorophenylmethylene)cyclohexyl]azetidine,
1-[2-(3,4-dichlorophenylmethylene)cyclohexyl]azetidine,
1-[2-(4-ethylphenylmethylene)cyclohexyl]azetidine,
1-[2-(4-trifluoromethylphenylmethylene)cyclohexyl]azetidine,
1-[2-(4-hydroxyphenylmethylene)cyclohexyl]azetidine,
1-[2-(4-carboxyphenylmethylene)cyclohexyl]azetidine, sodium salt,
1-[2-(3-methoxy-4-chlorophenylmethylene)cyclohexyl]azetidine,
1-[2-(4-ethoxycarbonylphenylmethylene)cyclohexyl]azetidine,
1-[2-(4-acetoxyphenylmethylene)cyclohexyl]azetidine,
1-[2-(4-hydroxymethylphenylmethylene)cyclohexyl]azetidine,
1-[2-(4-propionyloxymethylphenylmethylene)cyclohexyl]azetidine,
1-[2-(3,4-ethylenedioxyphenylmethylene)cyclohexyl]azetidine,
1-[2-(3-methoxymethylphenylmethylene)cyclohexyl]azetidine,
1-[2-(4-methoxycarbonylmethylphenylmethylene)cyclohexyl]azetidine,
1-[2-(4-phenylphenylmethylene)cyclohexyl]azetidine,
1-[2-(4-phenoxyphenylmethylene)cyclohexyl]azetidine,
1-[2-(4-benzylphenylmethylene)cyclohexyl]azetidine,
1-[2-(4-benzyloxyphenylmethylene)cyclohexyl]azetidine,
1-[2-(4-phenylethylphenylmethylene)cyclohexyl]azetidine,
1-[2-(4-phenylethenylphenylmethylene)cyclohexyl]azetidine,
1-[2-(4-phenoxymethylphenylmethylene)cyclohexyl]azetidine,
1-[2-(4-fluorophenoxyphenylmethylene)cyclohexyl]azetidine,
1-[2-(4-trifluoromethylbenzylphenylmethylene)cyclohexyl]azetidine,
1-[2-(4-methylbenzyloxyphenylmethylene)cyclohexyl]azetidine,
1-[2-(4-ethoxyphenylethylphenylmethylene)cyclohexyl]azetidine,
1-[2-(4-hydroxyphenylethenylphenylphenylmethylene)cyclohexyl]azetidine, and the like, or a pharmaceutically acceptable salt thereof.

A preferred subgeneric group of compounds of this invention are those of the formula III wherein each of $R_{50}$ and $R_{60}$ represents hydrogen or a substituent selected from the group consisting of a halogen having an atomic number of from 9 to 35, $C_1$ to $C_4$-alkyl, trifluoromethyl, hydroxy, $C_1$ to $C_2$-alkyloxy, phenoxy, and —CH($R_{10}$)—C(O)—O($R_{11}$) where $R_{10}$ and $R_{11}$ are as defined hereinabove, and acid addition salts, particularly pharmacologically acceptable acid addition salts, thereof.

An especially preferred compound example of formula III is one where each of $R_{50}$ and $R_{60}$ is hydrogen, namely (±)-(E)-1-[2-(phenylmethylene)cyclohexyl]azetidine. Other examples include:
1-[2-[(4-fluorophenyl)methylene]cyclohexyl]azetidine,
1-[2-[(3-fluorophenyl)methylene]cyclohexyl]azetidine,
1-[2-[(4-chlorophenyl)methylene]cyclohexyl]azetidine,
1-[2-[(3,4-dichlorophenyl)methylene]cyclohexyl]azetidine,
1-[2-[(3-fluoro-4-methoxyphenyl)methylene]cyclohexyl]azetidine,
1-[2-[(3,4-difluorophenyl)methylene]cyclohexyl]azetidine,
1-[2-[(3,4-dimethylphenyl)methylene]cyclohexyl]azetidine,
1-[2-[(4-hydroxyphenyl)methylene]cyclohexyl]azetidine,
1-[2-[(4-tert-butylphenyl)methylene]cyclohexyl]azetidine,
1-[2-[(4-isobutylphenyl)methylene]cyclohexyl]azetidine,
1-[2-[(4-acetoxyphenyl)methylene]cyclohexyl]azetidine,
1-[2-[[4-(ethoxycarbonylmethyl)phenyl]methylene]cyclohexyl]azetidine,
1-[2-[(3-hydroxy-4-methoxyphenyl)methylene]cyclohexyl]azetidine,
1-[2-[(3-methoxy-4-hydroxyphenyl)methylene]cyclohexyl]azetidine,
1-[2-[(4-phenoxyphenyl)methylene]cyclohexyl]azetidine, and the like, and the acid addition salts, particularly the pharmacologically acceptable salts, thereof.

Another preferred group of compounds of formula I of this invention are those of the formula IV (see formula pages) wherein $R_{61}$ represents benzyloxy ($-OCH_2C_6H_5$) or benzyloxy substituted on ring carbon atoms thereof by one or two substituents selected from the group consisting of halogen as defined above, trifluoromethyl, $C_1$ to $C_2$-alkyl, $C_1$ to $C_2$-alkyloxy and hydroxy, and acid addition salts, particularly pharmacologically acceptable salts, thereof. Representative examples of this subgroup of compounds show substantial antidepressant potency in standard laboratory animal tests. Examples of such compounds include:
1-[2-[[4-benzyloxy)phenyl]methylene]cyclohexyl]azetidine,
1-[2-[[5-(benzyloxy)phenyl]methylene]cyclohexyl]azetidine,
1-[2-[[4-(4-chlorobenzyloxy)phenyl]methylene]cyclohexyl]azetidine,
1-[2-[[4-(4-methylbenzyloxy)phenyl]methylene]cyclohexyl]azetidine,
1-[2-[[4-(3,4-dichlorobenzyloxy)phenyl]methylene]cyclohexyl]azetidine,
1-[2-[[4-[4-(trifluoromethyl)benzyloxy]phenyl]methylene]cyclohexyl]azetidine,
1-[2-[[4-(4-methoxybenzyloxy)phenyl]methylene]cyclohexyl]azetidine,
1-[2-[[4-(4-hydroxybenzyloxy)phenyl]methylene]cyclohexyl]azetidine,
and the like, and the acid addition salts, particularly the pharmaceutically acceptable acid addition salts thereof.

Another preferred group of compounds within formula I of this invention are those of formula V wheren $R_4$ represents $C_1$ to $C_2$-alkyl, 3-hydroxy, 3-($C_1$ to $C_2$-alkyloxy) or 3-($C_1$ to $C_2$-alkanoyloxy), and the acid addition salts, particularly the pharmaceutically acceptable acid addition salts, thereof.
Examples of such compounds include:
2-methyl-1-[2-(phenylmethylene)cyclohexyl]azetidine,
3-methyl-1-[2-(phenylmethylene)cyclohexyl]azetidine,
3-hydroxy-1-[2-(phenylmethylene)cyclohexyl]azetidine,
3-methoxy-1-2-(phenylmethylene)cyclohexyl]azetidine, and
3-acetoxy-1-[2-(phenylmethylene)cyclohexyl]azetidine, and pharmacologically acceptable salts thereof.

Another subgroup of compounds of formula I of interest for their mixed analgesic and antidepressant properties in animal tests are those of formula VI wherein $R_{70}$ is hydroxymethyl ($-CH_2OH$), $C_1$ to $C_4$-alkyloxymethyl, phenoxymethyl, carboxyl ($-COOH$), sodium and potassium salts of the carboxyl group, $C_1$ to $C_3$-alkyloxycarbonyl (esters), $C_2$ to $C_5$-alkanoyloxy ($-OC(O)-C_1$ to $C_4$-alkyl) and benzoyloxy ($-OC(O)-C_6H_5$) groups, and the like, and the acid addition salts, particularly the pharmacologically acceptable acid addition salts thereof.
Examples of such compounds include:
1-[2-[[4-(hydroxymethyl)phenyl]methylene]cyclohexyl]azetidine,
1-[2-[[4-ethoxymethyl)phenyl]methylene]cyclohexyl]azetidine,
1-[2-[[4-(pheoxymethyl)phenyl]methylene]cyclohexyl]azetidine,
1-[2-[(4-carboxyphenyl)methylene]cyclohexyl]azetidine,
1-[2-[(4-ethoxycarbonylphenyl)methylene]cyclohexyl]azetidine,
1-[2-[(4-carboxyphenyl)methylene]cyclohexyl]azetidine sodium salt,
1-[2-[[4-(propanoyloxy)phenyl]methylene]cyclohexyl]azetidine,
1-[2-[[4-(phenylcarbonyloxy)phenyl]methylene]cyclohexyl]azetidine, and the like, and the acid addition salts, particularly the pharmacologically acceptable acid addition salts thereof.

Another group of compounds of this invention, of interest primarily as chemical intermediates to other compounds of this invention are those free 2-amino compounds of formula I above wherein $R_2$ and $R_3$ are each hydrogen and the acid addition salts thereof. A few examples thereof include:
2-(phenylmethylene)cyclohexanamine,
2-[(4-trifluoromethylphenyl)methylene]cyclohexanamine,
2-[(3,4-dichlorophenyl)methylene]cyclohexanamine,
2-[(4-bromophenyl)methylene]cyclohexanamine,
2-[(4-methylphenyl)methylene]cyclohexanamine, and the like, and the acid addition salts thereof.

Another subgroup of compounds of this invention are those of formula I above, having the Claim 1 definitions, except that $R_2$ is hydrogen or $C_1$ to $C_2$-alkyl and $R_3$ is $C_1$ to $C_4$-alkyl, cyclopropyl, cyclobutyl, and the acid addition salts, particularly the pharmacologically acceptable acid addition salts thereof. A few representative examples thereof include:
N-ethyl-N-methyl-2-(phenylmethylene)cyclohexanamine,
N-(1,1-dimethylethyl)-2-(phenylmethylene)cyclohexanamine,
N-methyl-N-(1-methylethyl)-2-(phenylmethylene)cyclohexamine, N,N-dimethyl-2-[(4-phenoxyphenyl)methylene]cyclohexanamine, N,N-diethyl-2-[(4-benzylphenyl)methylene]cyclohexanamine, N-methyl-N-tert-butyl-2-[[4-(hydroxymethyl)phenyl]methylene]cyclohexanamine, N,N-diethyl-2-[(3,4-ethylenedioxyphenyl)methylene]cyclohexanamine, N-methyl-N-butyl-2-[(4-methoxymethyl)methylene]cyclohexanamine, N,N-dimethyl-2-(phenylmethylene)cyclohexanamine, N-methyl-N-ethyl-2-[(4-methoxyphenyl)methylene]cyclohexanamine, N-methyl-N-isopropyl-2-[(3-methoxy-4-chlorophenyl)methylene]cyclohexanamine, N-tert-butyl-2-[(4-acetoxyphenyl)methylene]cyclohexanamine, N,N-diethyl-2-[(4-fluorophenyl)methylene]cyclohexanamine, N-cyclopropyl-2-(phenylmethylene)cyclohexanamine, N-methyl-N-cyclobutyl-2-[(3,4-dichlorophenyl)methylene]cyclohexaneamine, and the like, and the acid addition salts thereof, particularly the pharmacologically acceptable salts thereof.

The following compounds, many of which have been made, are examples of compounds within the scope of this invention. Characterization data, e.g., melting point (mp) in degrees Centigrade or molecular weight (MW) determined by high resolution mass spectrometry (HRMS), are indicated for (except as noted) the (±)-(E)-isomer free base or the named salt thereof. The Roman numeral(s) from Schemes I–IX is (are) given to specify the route of synthesis.

1-[2-(phenylmethylene)cyclohexyl]azetidine which can also be named 1-[2-(benzylidenyl)cyclohexyl]azetidine, various salts recited below, I, IV, V;

1-[2-(phenylmethylene)cyclohexyl]azetidine, (Z)-isomer, MW: found 227.1670, calcd 227.1674, VIII;

1-[2-(phenylmethylene)cyclohexyl]azetidine, (+)-isomer, maleate, mp 115–116, $[\alpha]_D = +54°$ (5.12 mg/ml in methanol);

1-[2-(phenylmethylene)cyclohexyl]azetidine, (−)-isomer, maleate, mp 115–116; $[\alpha]_D = -53°$ (4.59 mg/ml in methanol);

1-[2-[[4-(trifluoromethyl)phenyl]methylene]cyclohexyl]azetidine, as the para-toluenesulfonate, mp 135–136, IX;

1-[2-[(4-fluorophenyl)methylene]cyclohexyl]azetidine, MW: found 245.1562; calcd 245.1580, IX;

1-[2-[(4-methoxyphenyl)methylene]cyclohexyl]azetidine paratoluenesulfonate, mp 114–115, II;

1-[2-[(3-methoxyphenyl)methylene]cyclohexyl]azetidine hydrochloride, mp 136–137, II;

1-[2-[(3-fluorophenyl)methylene]cyclohexyl]azetidine, MW: found 245.1576; calcd 245.1579, VI, IX;

1-[2-[(4-methylphenyl)methylene]cyclohexyl]azetidine, MW: found 241.1844; calcd 241.1830; V;

1-[2-[(3-hydroxyphenyl)methylene]cyclohexyl]azetidine, which can also be named as 3-[[2-(1-azetidinyl)cyclohexylidene]methyl]phenol, mp 160–165, III;

1-[2-[[4-(phenylmethoxy)phenyl]methylene]cyclohexyl]azetidine, mp 60–61, VI;

1-[2-[(3,4-dichlorophenyl)methylene]cyclohexyl]azetidine, MW: found 295.0892, calcd 295.0894, VI;

1-[2-[(3,4-dimethylphenyl)methylene]cyclohexyl]azetidine, MW: found 255.20106, calcd 255.19868, VI;

1-[2-[(4-chlorophenyl)methylene]cyclohexyl]azetidine, MW: found 261.12871, calcd 261.12841, V;

1-[2-[(3,4-difluorophenyl)methylene]cyclohexyl]azetidine, MW: found 263.14875, calcd 263.14854, VI;

1-[2-[(3-fluoro-4-methoxyphenyl)methylene]cyclohexyl]azetidine, MW: found 275.1698, calcd 275.1685, VI;

1-[2-[(4-hydroxyphenyl)methylene]cyclohexyl]azetidine, which can also be named 4-[[2-(1-azetidinyl)cyclohexyl]methylene]phenol, hydrochloride, mp 180–181, VI;

1-[2-[(3,4-dimethylphenyl)methylene]cyclohexyl]azetidine, maleate, mp 114–115, VI;

1-[2-[[3-methoxy-4-(phenylmethoxy)phenyl]methylene]cyclohexyl]azetidine, mp 78.5–80, VI;

1-[2-[[4-[(4-methoxyphenyl)methoxy]phenyl]methylene]cyclohexyl]azetidine, MW: found 363.21981, calcd 363.21853, VI;

1-[2-[[3,4-bis(phenylmethoxy)phenyl]methylene]cyclohexyl]azetidine, MW: found 439.25286, calcd 439.25111, VI;

1-[2-[[4-[(4-chlorophenyl)methoxy]phenyl]methylene]cyclohexyl]azetidine, MW: found 367.17196, calcd 367.17028, VI;

1-[2-[(4-acetoxyphenyl)methylene]cyclohexyl]azetidine, which can also be named as 4-[[2-(1-azetidinyl)cyclohexylidene]methyl]phenol, acetate ester, MW: found 285.1724, calcd 285.1729, VI;

1-[2-[[4-(1,1-dimethylethyl)phenyl]methylene]cyclohexyl]azetidine, which can also be named 1-[2-[4-(tert-butylphenyl)methylene]cyclohexyl]azetidine, MW: found 283.22929, calcd 283.22998, VI;

1-[2-(1,3-benzodioxol-5-ylmethylene)]cyclohexyl]azetidine, which can also be named 1-[2-[[(3,4-methylenedioxy)phenyl]methylene]cyclohexyl]azetidine, MW: found 271.157761, calcd 271.157218, VI;

1-[2-[[4-(hydroxymethyl)phenyl]methylene]cyclohexyl]azetidine which can also be named as 4-[[2-(1-azetidinyl)cyclohexylidene]methyl]benzenemethanol, MW: found 257.1773, calcd 257.1780, VI, succinate, mp 125–126, VI;

1-[2-[(3,4-dihydroxyphenyl)methylene]cyclohexyl]azetidine, which can also be named 4-[[2-(1-azetidinyl)cyclohexylidene]methyl]-1,2-benzenediol, MW: found 259.1572, calcd 259.1572, VI;

1-[2-[[4-(ethoxycarbonyl)phenyl]methylene]cyclohexyl]azetidine, which can also be named 4-[[2-(1-azetidinyl)cyclohexylidene]methyl]benzoic acid, ethyl ester, MW: found 299.1892, calcd 299.1885, VI;

1-[2-[(3-hydroxy-4-methoxyphenyl)methylene]cyclohexyl]azetidine, mp 168–169, VI;

1-[7-(phenylmethylene)-1,4-dioxaspiro[4.5]dec-8-yl]azetidine, MW: found 285.1733, calcd 285.1729, VII and then part of VI;

1-[2-[[4-[[4-(trifluoromethyl)phenyl]methoxy]phenyl]methylene]cyclohexyl]azetidine, mp 83°–84°, VI;

1-[2-[[4-(benzoyloxy)phenyl]methylene]cyclohexyl]azetidine, mp 124–125, VI;

1-[2-[(4-phenoxyphenyl)methylene]cyclohexyl]azetidine, MW: found 319.1943, calcd 319.1936, VI;

4-[[2-(1-azetidinyl)cyclohexylidene]methyl]-2-methoxyphenol, hydrochloride, mp 164–165;

1-[2-[[4-(2,2-dimethylpropanoyloxy)phenyl]methylene]cyclohexyl]azetidine, mp 113.5–114.5, VI;

1-[2-[[4-(2-phenylethyl)phenyl]methylene]cyclohexyl]azetidine, MW: found 331.2288, calcd 331.2300, VI;

1-[2-[[4-(phenylmethyl)phenyl]methylene]cyclohexyl]azetidine, maleate, mp 144–145, VI;

1-[2-[[4-[(3,4-dichlorophenyl)methoxy]phenyl]methylene]cyclohexyl]azetidine, MW: found 401.1328, calcd 401.1315, VI;

1-[2-[[4-(phenoxymethyl)phenyl]methylene]cyclohexyl]azetidine, MW: found 333.2101, calcd 333.2093, VI;

1-[2-[[4-[(4-methylphenyl)methoxy]phenyl]methylene]cyclohexyl]azetidine, mp 88–90, VII and then part of VI;

1-[2-[[4-(methoxycarbonyl)phenyl]methylene]cyclohexyl]azetidine, methanesulfonate, mp 183.5–184, VI;

1-[2-[(4-carboxyphenyl)methylene]cyclohexyl]azetidine, sodium salt, which can also be named 4-[[2-(1-azetidinyl)cyclohexylidene]methyl]benzoic acid, sodium salt, dihydrate, mp >300; and 1-[2-[[4-(2-phenylethenyl)phenyl]methylene]cyclohexyl]azetidine, mp 139.5–141.5, VI with an additional step as described hereinbelow and the like, and the pharmaceutically acceptable salts thereof.

The compounds of formula I above can be prepared by at least one of a series of processes which are somewhat related. The choice of process may depend upon the particular formula I compound being prepared. The processes are set forth in scheme or flowsheet form attached to the specification.

In general, the processes usually start with the selected unsubstituted or R-substituted $C_5$ to $C_8$-cycloalkanone such as cyclopentanone, cyclohexanone, cycloheptanone or cyclooctanone, or such cyclic ketones substituted, as indicated above with one methyl, ethyl, n-propyl or isopropyl groups, or with an ethylenedioxy or 1,3-propylenedioxy group bonded to carbon atom number four of a cyclohexene ring, e.g., 4-methylcyclopentanone, 3-methylcyclohexanone, 1,4-dioxaspiro[4.5]decan-8-one, 4-methylcycloheptanone, 2-methylcycloheptanone, 3-methylcyclooctanone, and 4-methylcyclohexanone. In general these cycloalkanones are known in the art or can be prepared by known methods. In some processes the selected R-substituted cycloalkanone is converted to an enamine such as the 1-(4-morpholinyl)cycloalk-1-ene by well-known methods.

A preferred process for making these compounds can start from a 1-morpholinyl-1-cycloalkene such as the appropriate substituted or unsubstituted 1-morpholinyl-1-cyclopentene, 1-morpholinyl-1-cyclohexene, 1-morpholinyl-1-cycloheptene and 1-morpholinyl-1-cyclooctene, with the selected unsubstituted or $R_1$-substituted benzaldehyde by using the procedure described by Birkofer et al. in Ber. 85:1495 (1962) which describes the preparation of 2-(phenylmethylene)cyclohexanone from 1-morpholinyl-1-cyclohexene. The $R_1$-substituted benzaldehyde reactants are knwon in the literature or can be prepared by known processes.

According to one process (Scheme I) to prepare azetidine compounds the selected 2-($R_1$-substituted-benzoyl)-R-substituted-cycloalkanone is reacted with the selected unsubstituted or $R_4$-substituted 3-amino-1-propanol with azeotropic removal of water to form a 2-($R_1$-substituted-benzoyl)-1-[(3-hydroxypropyl)amino]-R-substituted-cycloalk-1-ene, which enamine compound is catalytically hydrogenated, e.g. over platinum in ethanol solution, to provide the 2-[$R_1$-substituted-phenyl-(hydroxy)methyl]-N-(3-hydroxypropyl)-R-substituted-cycloalk-1-ylamine (generally with the substituents on the 1- and 2-positions of the cycloalkyl ring in a cis (same side of the ring) orientation). This phenyl(hydroxy)methyl compound is then dehydrated, e.g. by treatment with a concentrated acid such as hydrochloric acid for a time sufficient to form the 3-[N-[2-($R_1$-phenylmethylene)-R-cyclo]alkyl]-amino-$R_4$-1-propanol, which amino-alcohol is then treated with bromine and triphenylphosphine and heated for a time sufficient to effect cyclization to form the formula I azetidine compound. The formula I azetidine product can be converted to a variety of acid addition salts, either to assist extraction from its reaction mixture, for example, the oxalic acid salt, or thereafter to obtain a stable, crystalline salt form of the azetidine compound having enough bulk to be easily handled for preparing pharmaceutical drug forms of the compounds. Such salt forms include the succinate, hydrochloride, maleate, p-toluenesulfonate, fumarate and the 2-naphthalenesulfonate salt.

According to a variation of the above azetidine forming process (Scheme II) the 3-[N-[2-[($R_1$-phenyl)methylene]-R-cycloalkyl]amino]-$R_4$-1-propanol intermediate can be treated with a sulfonating agent, e.g., with chlorosulfonic acid, to form the sulfonic acid derivative, which can then be heated with a base, e.g. sodium hydroxide in water at up to the reflux temperature for a time sufficient to cyclize the compound to the azetidine.

When it is desired to effect de-etherification of an ether substituted compound such can be done (Scheme III) by subjecting the ether compound to appropriate acid treatment, e.g., with a strong aqueous hydrohalide acid such as hydrobromic acid and heat for a time sufficient to form the corresponding hydroxy substituted compound.

The free —$NH_2$ amino compounds within formula I may be prepared according to another process, outlined in flowsheet form in Scheme IV. This process route can also be optionally used to prepare the new azetidine derivative compounds of this invention. According to this process, the selected unsubstituted or substituted benzoylcycloalkanone is reacted with an appropriate amine, for example, with benzylamine to form the corresponding N-(2-benzoylcycloalk-1-enyl-N-benzylamine, which amine is then reduced and debenzylated to form the corresponding N-[2-[phenyl(hydroxy)methyl]-cycloalkyl]amine according to a procedure described by J. Szmuszkovicz, et al., *Journal of Organic Chemistry*, Volume 33, pages 3300–3313 (1967). The resulting hydroxymethyl amine is then dehydrated, e.g., with concentrated hydrohalic acid such as hydrochloric acid to form the corresponding N-[2-(phenylmethylene)cycloalkyl]amine. This amine can be recovered and used as such for pharmaceutical purposes or used as a chemical intermediate to form the corresponding azetidine by treatment of the amine with an appropriate 1,3-dihalopropane, or $R_4$-substituted 1,3-dibromopropane, 1,3-dibromo-2-methylpropane, 1,3-dibromo-2-methoxypropane, 1,3-dibromo-2-hydroxypropane, and the like, to form the azetidine ring in acetonitrile, N,N-dimethylformamide, or the like.

Using other selected $HNR_2R_3$ amines in place of benzylamine, this same process, Scheme IV, may be used to prepare the formula I amine compounds with $HNR_2R_3$ amines, when $R_2$ and $R_3$ are $C_1$ to $C_3$-alkyl or one of $R_2$ and $R_3$ is hydrogen and the other is $C_1$ to $C_4$-alkyl, cyclopropyl, cyclobutyl, 2-furylmethyl, 3-furylmethyl, benzyl, as above, or allyl. With such amine reactants, following Scheme IV, the formula I, $NR_2R_3$-amine forming process would stop after the dehydration step. The debenzylation step of Scheme IV is only used when it is desired to remove a benzyl group.

Alternatively, when the primary amine or the azetidine formula I compound is desired, the process of Scheme V can be used. According to this process the unsubstituted or substituted 2-benzoylcycloalkanone is treated with ammonium nitrate and ammonia under cooling conditions to form the corresponding N-[2-benzoylcycloalk-1-enyl]amine, which keto-cycloalk-1-enylamine is then treated with an alkali metal cyanoborohydride in THF in the presence of perchloric acid followed by an alkali metal borohydride in ethanol to convert the ketone group to an alcohol and saturate the ring double bond and form the corresponding N-[2-phenyl(hydroxy)methyl]cycloalkylamine, which hydroxy compound can then be dehydrated and converted to the corresponding N-[2-(phenylmethylene)cycloalkyl]amine compound by the above indicated procedures. The cyanoborohydride reaction conditions are carefully chosen so as to avoid hydrolysis of the vinylogous amide starting material.

Optionally, the resulting N-[2-(phenylmethylene)cycloalkyl] primary amine compounds can be converted to the corresponding azetidines by treatment of the primary amine with 1,3-dibromopropane or its equivalent 1,3-dihalo-$R_4$-propane reactant to form the corresponding $R_4$-azetidine compound.

A most generally preferred method for making most of the compounds of this invention is that according to the process of Scheme VI wherein the corresponding 2-(phenylmethylene)cycloalkanone is first prepared by reacting the corresponding R-cycloalk-1-enylmorpholine with the appropriate $R_1$-benzaldehyde to form directly the 2-($R_1$-phenylmethylene)-(R-cycloalkanone), which -cycloalkanone can then be treated with an alkali metal (such as sodium) cyanoborohydride and either ammonium acetate or a desired $HNR_2R_3$-acetic acid salt to form the corresponding N-[2-$R_1$-phenylmethylene)(R-cycloalkyl)]amine, which if it is a primary amine, can then be converted to the azetidine, by methods described in this specification.

To prepare compounds of formula I of this invention wherein $R_1$ is phenylethenyl, the process of Scheme VI is used, but an additional step is necessary. A mixture of 2-[(4-bromophenyl)methylene]cyclohexanone, styrene, triethylamine, palladium acetate, and tri-ortho-tolylphosphine is reacted in acetonitrile at 100° C. in a sealed tube according to the procedure described by J. E. Plevyak et al., *Journal of Organic Chemistry*, Volume 44, page 4078 (1979). The resulting 2-[[4-(2-phenylethenyl)-phenyl]methylene]cyclohexanone is then aminated as described for Scheme VI.

Compounds of the formula I wherein $R_1$ is —CH($R_{10}$)—C(O)$R_{11}$ and $R_{10}$ is $C_1$ to $C_3$-alkyl are prepared by alkylating the formula I compounds wherein $R_1$ is —CH$_2$—C(O)—O—($C_1$ to $C_3$-akyl) by well known methods. For example reacting the compound to be alkylated with lithium diisopropylamide at low temperature, for example, about −70° to about −78°, in tetrahydrofuran-hexamethylphosphoric triamide solvent mixture, and then reaction of this mixture with an appropriate alkyl halide (preferably an alkyl iodide) at similarly low temperature for a time sufficient to achieve alkylation produces the desired formula I compound wherein $R_{10}$ is $C_1$ to $C_3$-alkyl.

Another process which can be used to prepare the 2-(phenylmethylene)cycloalkanone starting materials is that outlined in Scheme VII. According to this process option, the unsubstituted or R-substituted cycloalkanone is reacted with a solution containing lithium diisopropylamide (prepared from diisopropylamine in a dry, inert atmosphere under cooling conditions and an alkyllithium compound such as n-butyllithium), followed by treatment of that solution with the selected $R_1$-substituted benzaldehyde ($R_1$ is not hydroxy) to form the corresponding 2-[$R_1$-phenyl(hydroxy)methyl]cycloalkanone which ketoalcohol is then recovered, if desired, and treated with a tertiary amine such as triethylamine or dimethylaniline, and the like, and an alkylsulfonyl halide such as methanesulfonyl chloride for a time sufficient to form the sulfonate derivative, and then treated with a basic agent such as 1,5-diazabicyclo[4.3.0]non-5-ene(DBN) to convert the sulfonate intermediate to the 2-($R_1$-phenylmethylene)cycloalkanone ($R_1$ is not hydroxy) starting material or intermediate, which can be further reacted as in Scheme VI to produce a compound of this invention.

When it is desired to prepare and separate the Z-isomer of a particular formula I amine or azetidine derivative compound the process variation of Scheme VIII can be used. According to this Scheme VIII process the selected cis-N-[2-($R_1$-phenyl)(hydroxy)methyl]cycloalkylamine can be dehydrated with aqueous strong acid, as indicated above (Scheme IV), to form the corresponding 2-(phenylmethylene)cycloalkylamine, from which a certain amount of the E-isomer separates easily, and leaving a mixture of the E- and Z-stereo isomers of the compound. The E- and Z-isomer mixture which remains after separating some of the E-isomer form after the acid dehydration step can be dissolved in an appropriate organic liquid solvent, such as diethyl ether, cooled and treated with an amide forming acid or anhydride such as trifluoroacetic anhydride for a time sufficient to form the corresponding trifluoroacetyl amide of the formula I amine, which amide reaction mixture can be neutralized with aqueous base such as aqueous sodium or potassium hydroxide to neutralize excess trifluoroacetic acid, washed, the solvents evaporated, and the residue amide chromatographed and fractions collected in the elution liquids to separate crops of the respective E- and Z-isomers of the formula I trifluoroacetylamide being prepared. After separation and recovery of the Z-isomer form of the formula I trifluoroacetylamide, such can be reconverted to the formula I amine by aqueous base treatment in an organic liquid medium for a time sufficient to remove the trifluoroacetyl group and to form the substantially pure Z-isomer form of the formula I amine. Optionally, the Z-isomer form of the formula I amine can then be treated with a 1,3-dihaloalkane, or 3-bromo-1-alkanol having at least three carbons in the alkylene chain, as above, to form the corresponding formula I azetidine derivative compound in its Z-isomer form, sometimes mixed with N,N-diallyl- and N-allyl-N-[2-(phenylmethylene)cycloalkyl]amine which are side reaction products, and which allyl-amine products can be separated by chromatography procedures to obtain the pure Z-isomer form of the formula I azetidine compound.

Another process for preparing formula I azetidine type compounds involves direct reaction between the selected azetidine and the selected unsubstituted or substituted 2-benzoylcycloalkanone, as summarized in Scheme IX. In such a process the selected 2-benzoylcycloalkanone is refluxed with the selected azetidine in benzene or other equivalent organic liquid diluent in the presence of an acid catalyst such as p-toluenesulfonic acid for a time sufficient to form the indicated hydroxymethyl azetidine intermediates, which can be used as such or crystallized and separated from its reaction mixture, and then said hydroxymethyl azetidine intermediate can be subjected to acidic dehydration, as described above, to form the corresponding 1-[2-(phenylmethylene)cycloalkyl]azetidine, which can be isolated from its reaction mixture by known methods, and, if desired, converted to an acid addition salt thereof for crystal formation. The $R_4$-substituted azetidines used in this process of Scheme IX are either known in the art or can be made by known methods. See for example J. A. Moore in "Heterocyclic Compounds with Three or Four-Membered Rings", A. Weisberger, Ed, Interscience, New York, 1964; Chapter VII, p. 898, Trimethyleneimine and a 1981 update of this review.

Examples of additional formula I amine and azetidine compounds which can be prepared by the above described methods are the following compounds, many of which have been made. Characterization data, e.g., melting point (mp) in degrees Centigrade or molecular weight (MW) determined by high resolution mass spectrometry (HRMS), are indicated for (except as noted) the $(\pm)$-(E)-isomer free base or the named salt thereof. The Roman numeral(s) from Schemes I–IX is (are) given to specify the route of synthesis.

3,3-dimethyl-1-[2-(phenylmethylene)cyclohexyl]azetidine, MW: found 255.2031, calcd 255.1987, II;

2-methyl-1-[2-(phenylmethylene)-cyclohexyl]azetidine, Isomer A hydrochloride, mp 166–168, IV, and Isomer B hydrochloride, mp 169–170, IV;

2,4-dimethyl-1-[2-(phenylmethylene)cyclohexyl]azetidine, Isomer A and Isomer B, obtained as mixtures, IV;

3-methyl-1-[2-(phenylmethylene)cyclohexyl]azetidine, maleate, mp 156–157, V;

3-methyl-1-[2-(3-fluorophenylmethylene)cyclohexyl]azetidine, 2,4-dimethyl-1-[[2-[4-(phenylmethoxy)phenyl]methylene]cyclohexyl]azetidine, 2-methyl-1-[[2-[4-(4-chlorophenylmethoxy)phenyl]methylene]cyclohexyl]azetidine, 2,4-dimethyl-1-[[2-[4-(4-methoxyphenylmethoxy)phenyl]methylene]cyclohexyl]azetidine, 2-methyl-1-[2-[(3,4-dichlorophenyl)methylene]-4-ethylenedioxycyclohexyl]azetidine, 1-[2-(phenylmethylene)cycloheptyl]azetidine, hydrochloride, mp 149–150, IX;

1-[2-[(4-fluorophenyl)methylene]cycloheptyl]azetidine,

1-[2-[(4-methoxyphenyl)methylene]cyclooctyl]azetidine,

1-[2-(phenylmethylene)cyclooctyl]azetidine,

1-[2-(phenylmethylene)cyclopentyl]azetidine, as well as the $R_2R_3N$-type of amine represented by N,N-dimethyl-2(phenylmethylene)cyclohexaneamine, hydrochloride mp 210–212, V;

N-ethyl-N-methyl-2-(phenylmethylene)cyclohexanamine, MW: found 229.1840, calcd 229.1830, IV;

2-(phenylmethylene)cyclohexylamine, hydrochloride hydrate mp 192–193.5, V (IV);

N,N-diethyl-2-(phenylmethylene)cyclohexanamine, hydrochloride mp 187–188, IV;

N-ethyl-N-methyl-2-[(2-methylphenyl)methylene]cyclohexanamine, hydrochloride mp 170–171.5, VII and VI;

N-cyclopropyl-2-(phenylmethylene)cyclohexanamine, hydrochloride mp 201–202, IV;

N,N-dimethyl-2-[[(3-trifluoromethyl)phenyl]methylene]cyclohexanamine, hydrochloride mp 188–189.5, VII and VI;

N-(n-propyl)-2-(phenylmethylene)cyclohexanamine, hydrochloride, mp 223–224, IV;

N,N-dimethyl-2-[(3-methylphenyl)methylene]cyclohexanamine, hydrochloride mp 196–197, VII and VI;

N-cyclopropyl-N-methyl-2-(phenylmethylene)cyclohexanamine, hydrochloride mp 192–193, IV;

N-methyl-N-isopropyl-(2-phenylmethylene)cyclohexanamine, hydrochloride mp 200–201, IV;

N-allyl-2-(phenylmethylene)cyclohexanamine, hydrochloride mp 193–194, IV;

N-(tert-butyl)-2-(phenylmethylene)cyclohexanamine, MW: found 243.1989, calcd, 243.1987, IV;

2-(phenylmethylene)cyclohexanamine, $(\pm)$-(Z)-isomer hydrochloride mp 214–215, V;

N-methyl-N-[2-(phenylmethylene)cyclohexyl]-2-furanmethanamine, MW: found 281.176939, calcd 281.177953, IV;

N-[2-(phenylmethylene)cyclohexyl]-2-furanmethanamine, maleate mp 162–163, V;

N-[2-(phenylmethylene)cyclohexyl]benzenemethanamine, MW: found 277.1837, calcd 277.1830, IV;

∞-methylene-N-[2-(phenylmethylene)cyclohexyl]benzeneethanamine, hydrochloride mp 165–166, V;

4-[[2-(dimethylamino)cyclohexylidene]methyl]benzoic acid, methyl ester, which can also be named N,N-dimethyl-N-[2-[(4-methoxycarbonylphenyl)methylene]cyclohexyl]amine, mp 219–220, VI;

2[(3,4-dimethylphenyl)methylene]-N,N-dimethylcyclohexanamine, MW: found 243.197240, calcd 243.198688, VI;

N,N-dimethyl-2-[[4-(phenylmethoxy)phenyl]methylene]cyclohexanamine, mp 65–66, VI;

2-[[4-(hydroxymethyl)phenyl]methylene]cyclohexylamine,

N,N-dimethyl-2-[[4-(3-phenylpropyl)phenyl]methylene]cyclopentanamine,

N-cyclopropyl-2-[[4-[(methoxycarbonyl)methyl]phenyl]methylene]cyclooctylamine,

N-allyl-N-[2-(phenylmethylene)]cycloheptanamine, MW: found 241.1840, calcd 241.1830, V;

N,N-dimethyl-N-[2-(phenylmethylene)]cycloheptanamine,

N,N-dimethyl-N-[2-(phenylmethylene)]cyclopentanamine, maleate mp 118–119, V; and the like, and the pharmaceutically acceptable salts of the free bases.

The methods of preparing the compounds of this invention are further exemplified by the following detailed examples, which are not intended as being limiting on the scope of the invention.

EXAMPLE 1

1-[2-(Benzylidenyl)cyclohexyl]azetidine and its Succinate Salt (Exemplifies morpholine enamine preparation and the process of Scheme IV)

A. Preparation of 2-Benzoylcyclohexanone through a 1-(1cyclohexen-1-yl)morpholine To a clean, dry, and inert 300 gallon reactor, there were added 450 g of p-toluene sulfonic acid monohydrate, 45.7 kg of morpholine via vacuum from a grounded drum on a scale, 44.6 kg of cyclohexanone via vacuum from a grounded drum on a scale and 90 liters of toluene via vacuum from a grounded drum on a scale.

The reactor was continuously vented with nitrogen gas, set for reflux, and cold water flow through the condenser. The mixture in the reactor was stirred for 0.5 hr and then the mixture was heated to reflux temperature (115°–120° C.). Water from reflux distillation condensation (about 13 liters) was collected by draining off the bottom of a reflux U-tube attached to the condenser.

The mixture was refluxed overnight. Any remaining water collected in the U-tube trap was drained in the morning. The mixture was concentrated under vacuum to an oil, releasing pressure steam and using free steam to heat the mixture. The crude oil concentrate of N-(1-cyclohexen-1-yl)morpholine was cooled in the reactor using cold water cooling under nitrogen atmosphere.

To the N-(1-cyclohexen-1-yl)morpholine (about 455 moles) crude oil concentrate, obtained as above, there was added 450 liters of methylene chloride. The resulting mixture was stirred and cooled to −10° C., using a brine-methanol cooling means in the reactor jacket. The reactor was rendered inert by evacuating and venting with nitrogen, and then 39.2 kg (54 liters) of triethylamine was pulled into the reactor by vacuum from a grounded drum on a scale. The reactor was vented with nitrogen and the small continuous nitrogen flow was maintained.

To a separate, clean, inert 30 gallon glass reactor there was added, via vacuum from a grounded drum on a scale, 42.2 kg of benzoyl chloride, using protective equipment. Then, while cooling and stirring the larger reactor mixture, the benzoyl chloride was delivered from the 30 gallon reactor to the larger (300 gallon) reactor through a rubber hose at a rate to maintain the pot temperature below −10° C. When the benzoyl chloride addition was completed, the mixture was stirred at −10° C. for two hr. The 30 gallon reactor was rinsed with water, drained and filled with 60 liters of water. While cooling this 30 gallon water filled reactor, 50.8 kg (60 liters) of concentrated hydrochloric acid (36 to 38% by weight of HCl in water) was added thereto by vacuum pulling through a polyethylene tube from a grounded drum on a scale. The operator should wear protective equipment—gloves, face shield, apron. The resulting, somewhat diluted, hydrochloric acid solution was transferred to the larger 300 gallon reactor via hose and gravity, while cooling the larger reactor (300 gallon) with cold water jacket means, and at a rate to keep the pot temperature under 30° C. Additional somewhat diluted hydrochloric acid solution (60 liter distilled water and 60 liter concentrated hydrochloric acid) is prepared and added to the larger (300 gallon) reactor until the pH of the reaction mixture therein reaches pH 1. Then the resulting acidified mixture is stirred for 2 hr after hydrochloric acid solution addition is complete.

Then the organic, methylene chloride liquid phase in the 300 gallon reactor was separated from the aqueous liquid phase by dropping the organic liquid phase into 100 liters of saturated aqueous sodium chloride solution in a separate 300 gallon open top tank.

The aqueous phase in the original 300 gallon reactor was then extracted with 140 liters of methylene chloride. The separated methylene chloride extract was then added to the same 300 gallon open top tank containing the original methylene chloride liquid reaction layer.

After discarding the (methylene chloride extracted) aqueous liquid phase from the original reactor, and flushing the reactor clean with water, and drying it, the contents of the 300 gallon open top tank were stirred and settled, and the methylene chloride liquid phase from the open top tank is separated and placed into a 300 gallon receiver. From this receiver and using a 36 in. stainless steel filter using filter cloth precoated with a layer of sodium sulfate, the methylene chloride was filtered into the original 300 gallon reactor. The filter cake was washed with methylene chloride.

The original 300 gallon reactor, containing the original methylene chloride solution of the reaction product and the methylene chloride washes, is set for distillation, using a 50° C. water jacket temperature, a cold water cooled condenser, a jet vacuum, and brine on the 300 gallon receiver vessel. The methylene chloride reaction mixture solution was concentrated to about 70 liter volume. An additional 70 liters of methylene chloride was added by vacuum pulling to this distilling reaction mixture and the mixture was reconcentrated to about 70 liters volume.

With the vacuum still on and using vacuum pull, 70 liters of methanol was added from a grounded drum. The vessel was vented with nitrogen gas, cooled with cold water cooling and stirred for 2 hr. The reactor vessel jacket was drained of cold water and the jacket was filled with cold brine solution to reduce the temperature of the mixture inside to 0° C.

The methylene chloride distillate was drained from the receiver (200 gallon vessel), and discarded. The solids produced in the reactor were filtered on a 36-in grounded filter. The filtrate was collected in the receiver. The solid filter cake was washed with cold (0° C.) methanol. The pale yellow solid filter cake was dried under vacuum (27 mm of Hg) with slight nitrogen gas flow at 35° C. The solid cake weight was 20.4 kg (33.6%) mp 90°–92° C.

The above filtrate was transferred back to the 300 gallon reactor and concentrated for a second crop of solids. This concentrated mixture was drained into a 20 gallon stockpot and yielded ultimately 4.7 kg (7.7% yield) of additional solids, mp 88°–91° C.

The total yield of 2-benzoylcyclohexanone from the above steps 1 and 2 was 41.3%.

B. Preparation of N-[2-(benzoyl)cyclohex-1-enyl)benzylamine

To a clean, inerted 50 gallon glass-lined reactor there was added 12.45 kg of 2-benzoylcyclohexanone, prepared as in Part A above. The vessel was closed, evacuated and vented with nitrogen gas to inert the vessel.

Using a vacuum there were drawn into the reactor 85 liters (73 kg) of toluene and 6795 g of benzylamine, followed by a rinse of 4 liters of toluene. The resulting mixture was heated to reflux with free steam and 930 ml of water distillate was removed via a U-tube condensing apparatus while refluxing at 95°–113° C. over 3.5 hr.

The reaction vessel was switched from reflux to distilling apparatus and 5 gallons of toluene were removed. The thus concentrated mixture was gradually cooled to 40° C. and then further concentrated under a jet vacuum, heating with 40° C. water until a yellow crystalline residue concentrate was obtained. Then 8 gallons of absolute ethanol was added from a grounded container and the resulting ethanol-diluted concentrate was stirred under nitrogen to effect dissolution of the crystalline solid, for the next step.

This N-[2-(benzoyl)cyclohexen-1-yl]benzylamine intermediate had a mp of 71°–73° C.

The IR spectrum showed peaks at 695, 750, 1135, 1260, 1275, 1290, 1300, 1495, 1530, 1570 and 1585 cm$^{-1}$.

The NMR spectrum (CDCl$_3$) showed peaks at 1.30–1.80 (m,4H), 2.20–2.50 (m,4H), 4.47 (d,J=6 Hz,2H) and 7.13–7.47(m,10H).

Anal. Calcd. for C$_{20}$H$_{21}$NO: C, 82.44; H, 7.26; N, 4.81 Found: C, 82.49; H, 7.42; N, 4.47

C. Preparation of 2-[hydroxy(phenyl)methyl]cyclohexylamine

A 17.9 kg lot of N-[2-(benzoyl)-cyclohexen-1-yl]benzylamine in ethanol solution from Step B above, was hydrogenated at 100 psig over 10% palladium on carbon (1800 g) in a 20 or 30 gallon autoclave. The reduction required 18 days for completion. The hydrogenation reaction was monitored periodically by thin layer chromatography (tlc) analyses using alumina GF plates (Analtech) and 5% methanol in methylene chloride. The plates were visualized with iodine. The reduction proceeds through the intermediate N-[[2(hydroxy)-phenylmethyl]cyclohexyl]benzylamine which was evident by the tlc methods.

The tlc analysis method showed evidence of the desired subtitled, fully reduced amine, and the intermediate, partially reduced benzylamine alcohol, as follows:

TLC (ALUMINA GF)

sub-Titled amine R$_f$=0.46 using 5% methanol in methylene chloride Intermediate amine R$_f$=1.0 in 5% methanol in methylene chloride Intermediate amine R$_f$=0.83 using 10% ethyl acetate in methylene chloride sub-Titled amine R$_f$=0.0 in 10 percent ethyl acetate in methylene chloride The reaction mixture was removed from the inerted autoclave with nitrogen pressure and the autoclave vessel was rinsed with absolute ethanol. The above hydrogenation reduction step was repeated on additional starting materials as many times as needed.

The resulting hydrogenated reaction mixtures (including rinses) were vacuum filtered through a bed of ethanol-wet Solka-floc filter aid on an 18 in stainless steel filter into a 100 gallon glass-lined reactor as a receiver for the filtrate. The filter cake (hydrogenation catalyst) was prevented from drying by washing the sides of the filter with ethanol from a wash bottle as needed. The filter cake was washed thoroughly with ethanol and then after changing receivers, the cake was washed thoroughly with water and the catalyst was recycled.

The filtrate solution in the glass reactor was concentrated to 10 gallons using jet vacuum and warm (about 35° C.) water in the jacket. The vessel was warmed to 50° C., as needed, to dissolve all solids. The resulting concentrate solution was transferred into holding bottles and the reactor was rinsed with 2.5 gallons of ethanol. The intermediate product amine was allowed to crystallize from ethanol at room temperature.

After several days of standing, the holding bottles, with their solid/ethanol contents were cooled to 0° C., the solids were collected and washed with cold (about 0° C.) ethanol. The solid was dried in vacuo at 35° C. to give 11.05 kg of 2-[hydroxy(phenyl)methyl]cyclohexylamine as pale yellow crystals, mp 105°–108° C., 44% yield.

The filtrate was concentrated to 5 gallons and cooled to obtain a second crop of the same amine, 1.75 kg, mp 106°–108° C., 7% yield. Further concentration of the filtrate to 2.5 gallons followed by cooling gave 1.23 kg (5% yield) of a crude product, mp 77°–85° C. Concentration of this mother liquor to dryness yielded 4.2 kg of a brown viscous oil, which by tlc analysis still contains a small amount of the desired 2-[hydroxy(phenyl)methyl]cyclohexylamine.

The overall crystalline yield of this primary amine was 56%.

D. Preparation of 2-(benzylidenyl)cyclohexylamine

To 14.03 kg of 2-[hydroxy(phenyl)methyl]cyclohexylamine in an inerted 300 gallon reactor, there was added 54 gallons (203 l) of water. From a grounded drum on a scale there was added 257 kg of concentrated hydrochloric acid while stirring, to obtain approximately 6N acid concentration.

The acid addition line was rinsed with water. The resulting mixture was heated to reflux using pressure steam (in the reactor jacket) and the reaction to dehydrate the starting material and convert it to the 2-(benzylidenyl)cyclohexylamine (2 isomers) product was followed by tlc analysis using silica gel GF plates and 5% methanol in methylene chloride containing a trace of ammonium hydroxide. When the reaction was complete, the mixture was cooled to 5°–10° C. The cooled mixture was cautiously rendered basic (pH 11) with 50% aqueous sodium hydroxide solution, drawn from a grounded drum, portionwise so that the temperature remains below 30° C. Then the mixture is cooled to 10°–15° C. The mixture was then extracted with methylene chloride (2×50 liters). The pH of the aqueous liquid layer was adjusted to 6.6–9.8 and discarded. The methylene chloride liquid extracts were combined in an open top tank and dried over sodium sulfate, and then filtered into a 30 gallon glass reactor and concentrated to dryness using jet vacuum and warm water (35° C.) heating. The methylene chloride distillate was discarded. To the concentrate residue there was added 15.4 kg (24 liters of Skellysolve ® B and the mixture was stirred to dissolve the reactor contents. The vessel is then seeded with the desired isomer of (2-benzylidenyl)cyclohexylamine and then cooled to −20° C. overnight to effect solid formation. The solid was filtered, washed with Skellysolve ® B and dried in a vacuum without heat. The yield of (±)-(E)-2-(benzylidenyl)cyclohexylamine was 6.0 kg, mp 46°–48.5° C. The filtrate was concentrated and cooled to obtain a second crop. 1.46 kg, mp 44°–46° C. The filtrate from this second crop was again concentrated to obtain a third crop, 77.9 g, mp 38°–42° C. The filtrate was saved for salvage of the Z isomer. The total yield of crystalline (±)-(E)-2-(benzylidenyl)cyclohexylamine was 59%.

E. Preparation of 1-[2-(benzylidenyl)cyclohexyl]azetidine

1. Acetonitrile Method—Preferred solvent; fewer byproducts

To a 500 ml one-neck flask fitted with a nitrogen inlet, condenser and magnetic stirrer, there was added 5.0 g of 2-(benzylideny)cyclohexylamine, 175 ml of acetonitrile, 7.5 g of potassium carbonate, and 6.0 g (3.0 ml) of 1,3-dibromopropane. The mixture was stirred at room temperature (23° C.) for three days, during which time a heavy colorless precipitate was produced. TLC analysis of the reaction mixture at that time indicated about 50–60% consumption of the 2-(benzylidenyl)cyclohexylamine (using silica gel GF plates and 5% methanol in methylene chloride containing 3 drops of concentrated ammonium hydroxide per 10 ml of solvent mixture, visualized with 254 nm ultraviolet light).

$R_f$ of 2-(benzylidenyl)cyclohexylamine=0.52
$R_f$ of 1-[2-(benzylidenyl)cyclohexyl]azetidine=0.72

The mixture was then heated to reflux overnight with efficient stirring under nitrogen to push the reaction more to completion. TLC analysis of the reaction mixture after 20 hr of such reflux heating indicated the reaction was 90–95% completed. The mixture was cooled to room temperature and filtered to remove the potassium bromide and potassium bicarbonate by-products. The filtrate was then subjected to a vacuum to remove the solvent and leave as residue 6.9 g of a yellow oil. This yellow oil, neat, was chromatographed on packed silica gel (184 g) and eluted therefrom in fractions with 5% methanol in methylene chloride. After a 350 ml forecut was discarded, 50 ml fractions were taken. Fractions 3 to 5 gave 0.7 g (11.4%) of yellow oil which is about 50% pure (±)-(E)-1-[2-(benzylidenyl)cyclohexyl]azetidine by tlc analysis. Fractions 6 to 12 gave 3.7 g (60.3% yield) of pure (±)-(E)-1-[2-(benzylidenyl)cyclohexyl]azetidine as a pale yellow oil.

2. N,N-Dimethylformamide (DMF) Method

To a stirred mixture of 6.5 g (0.035 mol) of 2-(benzylidenyl)cyclohexylamine and 9.7 g (0.070 mol) of potassium carbonate in 130 ml of dry DMF, there was added 3.5 ml (0.035 mol) of 1,3-dibromopropane via a syringe. The mixture was stirred at 25° C. for 42 hr, leaving only a small amount of unreacted 2-benzylidenylcyclohexylamine by tlc analysis using silica gel GF plates and 5% methanol in chloroform containing a trace of ammonium hydroxide as solvent. The reaction mixture was poured into saturated brine and extracted with three 200 ml portions of ethyl ether. The combined organic liquid layers were washed with four 200 ml portions of cold water before drying the organic layer over sodium sulfate. Filtration of the dried organic layer and removal of solvent in vacuo afforded 8.3 g of yellow oil. Chromatography of this yellow oil on 250 g of silica gel packing, eluting with 5% methanol in methylene chloride gave nine 100 ml fractions.

Fractions 3 to 9 on combination gave 5.0 g (63%) yield of (±)-(E)-1-[2-(benzylidenyl)cyclohexyl]azetidine contaminated with a small amount of polar impurities.

F (Optional)

Preparation of (±)-(E)-1-[2-(benzylidenyl)cyclohexyl]azetidine, succinate (1:1) salt A 3.7 g portion of the 1-[2-(benzylidenyl)cyclohexyl]azetidine yellow oil from Step E above, is dissolved in 12 ml of dry methanol with stirring. Then 1.92 g of succinic acid is added in portions (with cooling if this salt formation step is done on a large enough scale to produce heat) with stirring. After dissolution of the succinic acid, anhydrous ethyl ether is added slowly with stirring until the mixture is slightly cloudy (50 ml). The resulting mixture is seeded with crystals of 1-[2-(benzylidenyl)cyclohexyl]azetidine succinate salt (from previous small batches). Crystallization began immediately at room temperature. The mixture was cooled to −20° C. overnight, filtered to collect crystals of (±)-(E)-1-[2-(benzylidenyl)cyclohexyl]azetidine succinate salt which were washed with anhydrous ethyl ether. The washed crystals were dried in vacuo at room temperature to constant weight. The yield of this salt was 4.9 g (87% yield), mp 145°–147° C.

The structure of the monohydrochloride hydrate of (±)-(E)-1-[2-(benzylidenyl)cyclohexyl]azetidine was confirmed by x-ray analysis.

EXAMPLE 2

1-[2-(benzylidenyl)cyclohexyl]azetidine and Its Maleate Salt (Exemplifies the process of Scheme I)

A. Preparation of cis-N-(3-hydroxypropyl)-N-[2-[hydroxy(phenyl)methyl]cyclohexyl]amine To a 30 gallon reactor there was added 8,040 g of 2-benzylocyclohexanone. The reactor was closed and inerted with nitrogen. The reactor vessel was evacuated and then 58 liters of toluene were added from a grounded drum. Then 3,042 g of 3-amino-1-propanol were added from bottles. The reactor was set for refluxing with a nitrogen atmosphere. The mixture was heated at reflux for 4 hr while collecting about 700 ml of water from a U-tube trap. (Distillation had been started with free steam. When distillation stopped, heating was switched to pressure steam at 120° C.). The reaction mixture was cooled to 30° C. and concentrated in vacuum to a yellow solid. The solid residue was redissolved in 80 liters of absolute ethanol in preparation for the hydrogenation to follow. The crude ethanolic solution in the reactor was placed in a pressure autoclave with 500 g of platinum oxide. The mixture was stirred overnight at room temperature with 50 psig of hydrogen. The reaction mixture was filtered to remove catalyst and rinsed with ethanol. The filtrate was evaporated to leave an oil as residue in a 50 gallon glass reactor. The oil was stirred with 60 liters of 10% (v/v) acetic acid in water, and then 60 liters of technical grade ether was added and stirring was continued for ten minutes. The liquid layers were separated and the aqueous layer was basified with about 24 liters of 20% sodium hydroxide to pH 11. The aqueous layer was extracted with 4×10 liters of methylene chloride. The combined organic liquid layers were washed with 20 liters of deionized water and once with 20 liters of saturated brine solution. The organic liquid layer was separated and dried over sodium sulfate. The mixture was filtered to remove solids and concentrated to an oil. The oily mixture was cooled with stirring and then mixed with 6 liters of absolute ethyl ether. The resulting solution was seeded (with an authentic sample from a small reaction) to crystallize the intermediate sub-titled product. The crystalline material was filtered and dried in a vacuum. The crude weight yield was 4,735 g.

The filtrate was concentrated to a small volume to give a second crop of crystals, which were filtered, rinsed with ethyl ether and dried in a vacuum. The yield of the sub-titled methanol derivative was 717 g (crude). A 500 g portion of the crude sub-titled methanol derivative was dissolved in 1 liter of methylene chloride, filtered to remove solid impurities. The filtrate was stirred while 2 liters of Skellysolve ® B was added slowly, the mixture was cooled and filtered again to separate the solid, purified sub-titled methanol derivative product, 402 g, mp 87°–92° C., TLC analysis indicates greater than 98% single spot material, which is usable in the next step. The TLC analysis was done using silica dioxide plates with 10% methanol in methylene chloride (as developing solvent). The mother liquors were concentrated and helf for purification.

B. Preparation of N-(3-hydroxypropyl)-N-[2-(benzylidenyl)-cyclohexyl]amine

In a 5 liter, 3-necked, round bottom flask there were combined 402 g of cis-2-[N-(3-hydroxypropyl)amino]-α-phenylcyclohexanemethanol, from Part A above, and 2,010 ml of concentrated hydrochloric acid. The mixture was stirred with steam heat (temperature, about 95° C.) for 2 hr. The mixture was cooled in an ice bath and basified with 20% sodium hydroxide solution to pH 10. The resulting aqueous mixture was extracted with 3×2 liters of methylene chloride. The methylene chloride extracts were separated from the aqueous phase and combined and washed with 2 liters of deionized water followed by 2 liters of saturated sodium chloride solution. The organic liquid phase was separated from the aqueous phase and dried over sodium sulfate, filtered and concentrated to an oil substantially free of solvents), weighing 383.5 g. Tlc analysis indicated sufficient purity of the sub-titled amine derivative to use in the next step.

C. Preparation of 1-[2-(benzylidenyl)cyclohexyl]azetidine

To a 3-liter, 3-necked flask equipped with a stirrer, thermometer, small addition funnel, placed in a cooling bath, there were added 1200 ml of acetonitrile and 109.6 g of triphenylphosphine. The mixure was stirred with cooling from an ice/water bath at 10° C. To the cooled solution there were added 66.8 g of bromine over 10 min at a rate sufficient to keep the temperature of the mixture between about 10°–15° C. When the bromine addition was completed, the cooling bath was replaced with a steam bath and the reaction mixture was heated to 30° C. At this temperature slow addition of 102 g of N-(3-hydroxypropyl)-N-[2-(benzylidenyl)cyclohexyl]amine from the previous step, dissolved in 255 ml of acetonitrile was accomplished. Heating of the mixture was continued up to reflux and the temperature was held at reflux temperature for 4 hr and then at ambient temperature overnight. Progress of the reaction was checked by tlc analysis of reaction mixture samples using 10% methanol in methylene chloride solution on silicon dioxide coated plates. The reaction mixture was evaporated to dryness on a rotary evaporator. The residue oil was redissolved in 500 ml of technical grade ethyl ether plus 500 ml of water, and the mixture was basified with 120 ml of 20% sodium hydroxide solution. Precipitated solids were removed and discarded. The liquid ether layer was separated and saved. The aqueous layer was extracted with 250 ml of fresh absolute technical grade ethyl ether. The aqueous layer was separated and discarded. The liquid ether fractions were combined and washed with (1) 500 ml of deionized water, (2) 500 ml of saturated sodium chloride solution, and then dried over magnesium sulfate, filtered and the liquid ether solvent was evaporated on a rotary evaporator leaving an oil residue. To this oil there was added 2 liters of absolute ethyl ether plus 200 ml of methylene chloride and the mixture was stirred and filtered to obtain 156 g of a solid gummy material. The filtrate was evaporated to dryness and the residue was heated with 1 liter of 20 percent sodium hydroxide solution for six hours. The mixture was cooled, stirred and mixed with 500 ml of absolute ethyl ether, filtered to remove solids (which were discarded). The aqueous layer was separated from the organic ether liquid layer and extracted with 2×500 ml portions of absolute ethyl ether. The combined ether extracts were evaporated to near dryness and filtered to remove solids (which were discarded). The ether filtrate was evaporated to a crude oil (weighing 92 g) and chromatographed as a methylene chloride solution through a 2 in×15 ft column packed with silica gel (4 kg) packing with 1 percent ethanol in methylene chloride. The column was eluted with 20 liters of 2% ethanol in methylene chloride, 40 liters of 5% ethanol in methylene chloride and 20 liters of 7% ethanol in methylene chloride. The chromatography liquid fractions were evaluated by tlc analysis using 10% ethanol in methylene chloride. The fractions collected and the tlc evaluation results were as follows:

| Fraction No. | Fraction Size | TLC Evaluation | Weight |
| --- | --- | --- | --- |
| 1–9 | 3.5 liters | Impurities (discard) | |
| 10 | 2 liters | Mixture with Product | 20 g |
| 11–22 | 2 liters | Product | 45 g |
| 23 | — | Impurities (discard) | — |

The fractions 11 to 22 were combined and evaporated as the (±)-(E)-isomer of the sub-titled product, 45 g of one spot TLC material.

D. Preparation of (±)-(E)-1-[2-(benzylidenyl)cyclohexyl]azetidine, Maleate Salt; also named (±)-(E)-1-[2-(phenylmethylene)cyclohexyl]azetidine butanedioate To a solution of 59.6 g of the 1-[2-(phenylmethylene)-cyclohexyl]azetidine, prepared as described in Part C hereinabove in 60 ml of methanol, there was added a solution of 29.4 g of maleic acid in 95 ml of methanol while stirring. The mixture was stirred for 5 min and then diluted with 175 ml of ethyl ether and cooled in an ice bath to crystallize out the solid salt. The solid was collected on a filter and recrystallized twice from a mixture of 400 ml of methanol and 400 ml of ethyl ether to leave 56 g of the sub-titled salt, mp 160°–161° C. of profile quality drug salt. The mother liquors were held to recover more sub-titled salt product therefrom.

EXAMPLE 3

Dehydration of cis-N-(3-hydroxypropyl)-N-[2-[hydroxy(phenyl)methyl][cyclohexyl]amine. Preparation of N-(3-hydroxypropyl)-N-[2-(phenylmethylene)cyclohexyl]amine A mixture of 2.5 g (9.5 mmoles) of cis-N-(3-hydroxypropyl)-N-[2-[hydroxy(phenyl)methyl][cyclohexyl]amine, 10 ml of toluene and 6.45 g of 48% v/v aqueous hydrogen bromide solution was stirred and heated on a steam bath for 3.5 hr. The resulting solution was cooled, basified with 20% sodium hydroxide solution and extracted with chloroform. The chloroform extract was washed with water, and saturated sodium chloride solution and then dried over magnesium sulfate and evaporated. The residue, 2 g, was chromatographed by high pressure liquid chromatography (HPLC) procedures using a Merck silica gel, size C column and 10% v/v methanol/in chloroform/1% v/v ammonium hydroxide mixture as eluting liquid, collecting 20 ml fractions. Fractions 1 to 14 gave no product material. Fractions 15 to 25 gave 0.686 g (30% yield) of (±)-(E)-1-[2-(phenylmethylene)cyclohexyl]azetidine, which was identified by NMR analysis comparison with the NMR of standard, authentic compound. Fractions 26 to 31 gave 0.25 g of a mixture, and fractions 32 to 50 gave 0.286 g of N-(3-hydroxypropyl)-N-[2-(phenylmethylene)cyclohexyl]amine which was identified by NMR comparison with a known standard sample, and also by conversion to its hydrochloride salt which was identical to a standard sample by NMR, UV and IR spectral analysis comparisons.

EXAMPLE 4

Preparation of
(±)-(E)-1-[2-(phenylmethylene)cyclohexyl]-azetidine.
(Exemplifies the process of Scheme I.)

A. Preparation of N-(3-hydroxypropyl)-N-[2-[hydroxy(phenyl)methyl]-cyclohexylamine A mixture of 2-benzoylcyclohexanone, 101.1 g (0.5 mole), 3 amino-1-propanol, 38.3 g (0.51 mole) and 750 ml of benzene was refluxed for 4 hr using an azeotropic separator. A total of 10.5 ml of water was collected. The resulting solution was evaporated and the residue was dissolved in ethanol and hydrogenated in three portions, each containing 200 ml of ethanol and 2.5 g of platinum dioxide during 18.5 hr employing initial pressure of about 50 psig of hydrogen. The mixture was filtered, evaporated and the residue stirred with 700 ml each of 10% aqueous acetic acid and diethyl ether. The acid liquid layer was separated, cooled, basified with 20% sodium hydroxide in water solution and extracted with methylene chloride. The methylene chloride extract was washed with water, then with saturated sodium chloride in water solution, and then dried using magnesium sulfate, and the solvent evaporated. The residue (100 g) titled intermediate, was converted to its hydrochloride in a methanol/diethyl ether 50:50 v/v mixture to give 85.9 g of a N-(3-hydroxypropyl)-N-[2-(phenyl(hydroxy]methyl)cyclohexylamine hydrochloride, mp 243°–244° C., which was unchanged on recrystallization. A second crop of this salt, 8.5 g, had a melting point of 237°–239° C. The infrared (IR), nuclear magnetic resonance (NMR) and mass spectral analyses were consistent with this named intermediate compound.

Anal. Calcd for $C_{16}H_{25}NO_2 \cdot HCl$ C, 64.08; H, 8.74; Cl, 11.83; N, 4.67 Found: C, 64.26 H, 9.03; Cl, 11.88; N, 4.63.

B. Preparation of 3-[[2-(phenylmethylene)cyclohexyl]amino]-1-propanol, and its hydrochloride A mixture of N-(3-hydroxypropyl)-N-[2-[phenyl(hydroxy)methyl]cyclohexyl]amine, from step (a) above, 50 g (0.19 mole) and 250 ml of concentrated hydrochloric acid was heated on a steam bath for 1.5 hr. The resulting solution was cooled in ice, basified with 20% aqueous sodium hydroxide solution and the product was extracted well with diethyl ether. The ether extract was dried with magnesium sulfate and evaporated to give 45.3 g of N-(3-hydroxypropyl)-N-[2-(phenylmethylene)cyclohexyl]amine, as an oil, which was used directly in the next preparative step. However, a portion of this amine oil was converted to its hydrochloride in methanol with a diethyl ether solution of hydrogen chloride and the salt was crystallized from the methanol/diethyl ether mixture, mp 175°–177° C. The IR, UV and NMR spectra were consistent.

Anal. Calcd for $C_{16}H_{23}NO \cdot HCl$ C, 68.19; H, 8.38; Cl, 12.58; N, 4.97% Found: C, 67.80; H, 8.70; Cl, 12.57; N, 4.72%.

This compound can also be named 3-[(2-phenylmethylene)cyclohexyl]amino-1-propanol, or N-(3-hydroxypropyl)-N-[2-(phenylmethylene)cyclohexyl]amine, and its hydrochloride.

C. Preparation of 1-[2-(phenylmethylene)cyclohexyl]-azetidine

To a suspension of 10.75 g (0.041 mole) of triphenylphosphine in 120 ml of acetonitrile there was added 6.55 g or 2.9 ml (0.041 mole) of bromine while keeping the temperature at 10°–15° C. The cooling ice bath was removed from around the reaction vessel and the thick suspensiion therein was treated with 10 g (0.041 mole) of the N-(3-hydroxypropyl)-N-[2-(phenylmethylene)cyclohexyl]amine, from step B above in 25 ml of acetonitrile. The resulting yellow solution was heated on a steam bath for 19 hr and then evaporated. The residue was dissolved in a water/diethyl ether mixture and the resulting mixture was basified with 20% aqueous sodium hydroxide solution. The ether layer was separated, washed with water, saturated sodium chloride solution and then dried over magnesium sulfate and evaporated. The residue was treated with diethyl ether and filtered to separate solid triphenylphosphine, 4 g, mp 151°–152° C. The filtrate was evaporated and the residue chromatographed on 770 g of silica gel using 1% methanol in chloroform mixture as eluent. Fraction 1 (750 ml) gave no product. Fractions 2 to 63 (30 ml each from now on) gave nothing. Fractions 64 to 68 gave 0.29 g of triphenylphosphine. Fractions 69 to 71 gave 0.125 g of mixture. Fractions 72 to 179 gave 6.2 g (67% yield) of (±)-(E)-N-[2-(phenylmethylene)cyclohexyl]azetidine as a yellow oil, one spot on thin layer chromatography (tlc) silica gel using 10% methanol in chloroform solution as developing liquid. The UV and NMR spectra were consistent with this named product. The succinic acid salt of this azetidine derivative compound was prepared in a methanol/diethyl ether mixture, to give the succinate salt, mp 144°–145° C., which was unchanged upon recrystallization. The UV and IR spectra were consistent for this salt.

Anal. Calcd. for $C_{16}H_{21}N \cdot C_4H_6O_4$ C, 69.54; H, 7.88; N, 4.06% Found: C, 69.29; H, 7.75; N, 3.93%.

This (±)-(E)-N-[2-(phenylmethylene)cyclohexyl]azetidine also formed other crystalline salts: the hydrochloride (hydrate, mp 146°–147.5° C.), maleate, tosylate (mp 75°–77° C.), fumarate, and napsylate salts.

EXAMPLE 5

1-[2-[(4-methoxyphenyl)methylene]cyclohexyl]azetidine (Exemplifies the process of Scheme II.)

Chlorosulfonic acid was added dropwise during 7 min to a solution of N-(3-hydroxypropyl)-N-[2-(4-methoxyphenylmethylene)cyclohexyl]amine, 5 g (0.017 mole) in 325 ml of diethyl ether keeping the temperature at about 3° C. with cooling. The mixture was then stirred at this 3° C. temperature for 30 min and then at room temperature for 2 hr to ensure complete reaction. The resulting suspension was filtered and the solid washed with diethyl ether. The solid was added to a cold solution of 6.5 g of sodium hydroxide in 50 ml of water and the mixture was heated at 95° C. for 2 hr, then cooled in ice, saturated with solid sodium hydroxide and extracted with chloroform. The chloroform extract was dried with magnesium sulfate and evaporated. The residue was chromatographed on a Merck silica gel size C column using an 8% v/v methanol in chloroform solution containing 1% v/v ammonium hydroxide solution mixture as eluent. Elution of the residue loaded column with 560 ml of this mixture gave no material. The next 500 ml gave 0.41 g of (±)-(E)-1-[2-[(4-methoxyphenyl)methylene]cyclohexyl]azetidine as an oil. The NMR was consistent for this named product. A crystalline p-toluenesulfonate salt was prepared, mp 114°–115° C.

EXAMPLE 6

1-[2-[(3-hydroxyphenyl)methylene]cyclohexyl]azetidine (Exemplifies the process of Scheme III.)

A mixture of 1.1 g of (±)-(E)-N-[2[(3-methoxyphenyl)methylene]cyclohexyl]azetidine, prepared by analogy to the preparation of the 4-methoxy compound of Example 5, and 5 ml of 48% hydrogen bromide in water solution was stirred and heated at 95° C. for 2.75 hr. The resulting mixture was cooled and extracted with diethyl ether. The ether extract was dried with magnesium sulfate and evaporated to give 0.8 g of N-[2-[(3-hydroxyphenyl)methylene]cyclohexl]azetidine as an oil which deposited as crystals upon standing overnight. Filtration with diethyl ether gave 0.21 g of this 3-hydroxyphenyl compound as a pale yellow solid. The UV, IR, mass spectrum and NMR analysis indicated the named product was present. Gas chromatography (GC) analysis indicated that this product was a mixture containing about 92% of (±)-(E)-1-[2-[(3-hydroxyphenyl)-methylene]cyclohexyl]azetidine, mp 160°–165° C. and 8% of the starting 1-[2-(3-methoxyphenyl)methylene]-cyclohexyl]azetidine, mp 136°–137° C.

Other compounds within the scope of the invention and processes for preparing them from known or preparable starting materials are illustrated by the following detailed Examples.

EXAMPLE 7

1-[2-[(4-methylphenyl)methylene]cyclohexyl]azetidine (Exemplifies the process of Scheme V.)

A. Preparation of 2-(p-toluoyl)-cyclohex-1-en-1-ylamine

Ammonia gas was bubbled into a cooled flask containing a suspension mixture of 2-p-toluoylcyclohexanone (21.6 g, 0.1 mole) and 8.8 g (0.11 mole) of ammonium nitrate until 17 g (1 mole) of ammonia was absorbed. The flask was stoppered and the mixture stirred for 30 min when a solution resulted. The flask and its mixture was allowed to stand overnight and the resulting brown solution was evaporated. The residue was extracted with boiling diethyl ether, 4×250 ml portions, filtered, and the extract was concentrated until crystallization began in the hot, and the mixture was allowed to cool. A total of 10 g of pale yellow needle crystals was obtained, mp 130°–131° C. A second crop of 6.35 g, mp 129°–130.5° C., for a total of 76% yield was obtained. The UV, mass spectrum and NMR spectra were consistent with the sub-titled intermediate amine.

Anal. Calcd. for $C_{14}H_{17}NO$: C, 78.10; H, 7.56; N, 6.51% Found: C, 77.92; H, 8.08; N, 6.32%.

B. Preparation of N-[2-[4-methylphenyl(hydroxy)methyl]cyclohexyl]amine

A solution of (2-amino-1-cyclohexen-1-yl)(4-methylphenyl)methanone, from step A above, 14 g, 0.065 mole) in 350 ml of tetrahydrofuran (THF) was cooled to −5° C. and then 9.3 g (0.065 mole) of 70% v/v aqueous perchloric acid ($HClO_4$) was added dropwise. Then a solution of sodium cyanoborohydride ($NaBH_3CN$), (16.3 g, 0.26 mole) in 50 ml of methanol was added. The resulting mixture was stirred at room temperature for 20 hr and basified with sodium hydroxide. The methanol and THF were evaporated off, and the residue was extracted well with diethyl ether. The ether extract was washed well with water and then with saturated aqueous sodium chloride solution and then dried with magnesium sulfate and evaporated. The resulting yellow oil (14.2 g) was dissolved in 100 ml of ethanol, cooled and treated with a solution of 14 g of sodium borohydride ($NaBH_4$) in 200 ml of ethanol. After 72 hr at room temperature the mixture was evaporated, taken up in a water/diethyl ether mixture, the ether extract separated, and the ether extract was washed once with water, discarding the water, and then the ether extract was extracted with three 75 ml portions of 10% aqueous hydrochloric acid solution. The acid extracts were combined and backwashed with diethyl ether, discarding the ether, and the acid extract was cooled, basified with sodium hydroxide, and extracted with diethyl ether. The ether extract was washed with water and then with saturated aqueous sodium chloride solution, dried over magnesium sulfate and evaporated to give 8.5 g of above sub-titled amine as a yellow oil. The IR spectrum thereof showed the absence of the carbonyl group (—C(O)—) absorption. The UV spectrum showed the absence of extended conjugation. The mass spectrum showed the desired M+219 ion as a major component. The NMR spectrum ($CDCl_3$ standard) was compatible with the isomeric mixture of amino-alcohols and showed three types of —CHOH at 5.0(s), 4.7 (d,J=2 Hz), and 4.4 (d,J=4 Hz).

C. Preparation of N-[2-(4-methylphenyl)methylene]cyclohexylamine.

An 8.3 g portion of the above step B amino alcohol and 83 ml of concentrated hydrochloric acid was stirred and heated on a steam bath for 1.5 hr, cooled, basified with 20% sodium hydroxide in water solution and extracted well with diethyl ether. The ether extract was washed with water, and then with saturated aqueous sodium chloride solution, dried with magnesium sulfate and evaporated. The resulting oil, 8 g, distilled using an oil-jacketed flask and the fraction boiling at 150°–160° C. (0.8 mm Hg) was collected, and weighed 3.21 g. Gas chromatography (GC) analysis (1% QF-1 column) showed two peaks: 72.7% at 3.17 min and 27.3% at 2.75 min, corresponding to E and Z isomers of N-[2-[(4-methylphenyl)methylene]cyclohexyl]amine. The NMR ($CDCl_3$) of this amine product showed two types of vinyl hydrogen at delta 6.4 and delta 6.2 (a ratio of about 7:1). The above amine oil was crystallized from petroleum ether (bp 30°–60° C.) to give 0.68 g of the crystalline E isomer form of the N-[2-(4-methylphenyl)-methylene]cylohexyl]amine, mp 94°–96° C. Gas chromatography (GC) analysis of this material showed one peak. The high resolution mass spectrum molecular weight found was 201.1526. The calculated molecular weight for this compound, $C_{14}H_{19}N$ is 201.1517. The UV and NMR spectral analyses were consistent with this named compound. The hydrochloride salt of this amine was formed with ethereal hydrogen chloride, and was crystallized from a methanol/diethyl ether mixture, mp 225°–226° C., U.V. $\lambda max(\epsilon)245(15,900)$, mass spectrum $M+201$.

Anal. Calcd for $C_{14}H_{19}N \cdot HCl$ C, 70.72; H, 8.98; Cl, 14.91; N, 5.89% Found: C, 70.73; H, 8.83; Cl, 14.48; N, 6.08%.

D. Preparation of 1-[2-[4-methylphenyl)methylene]-cyclo-hexyl]azetidine

A mixture of N-[2-[4-methylphenyl)methylene]cyclohexyl]amine, from step C above, 0.64 g (3.2 mmol) with 1.28 g (6.4 mmol) of 1,3-dibromopropane and 0.88 g (6.4 mmol) of potassium carbonate in 20 ml of ethanol as refluxed 18 hr, evaporated and the residue was taken up in a water/diethyl ether mixture. The aqueous layer was separated and saturated with solid potassium hydroxide and extracted with diethyl ether. The ether extract was washed with saturated sodium chloride solution, dried with magnesium sulfate and evaporated. The residue, 0.67 g, was chromatographed using a HPLC Merck C silica gel column using a 3% methanol in chloroform solution containing 0.5% ammonium hydroxide mixture as eluent. Elution with 620 ml of this eluting mixture gave mixtures of products containing the N-allyl derivative of the starting N-[2-[(4-methylphenyl)methylene]cyclohexyl]amine. Elution of the column contents with 5% methanol in chloroform containing 0.5% ammonium hydroxide (240 ml) gave no product. The next 540 ml gave 180 mg of $(\pm)$-(E)-1-[2-[(4-methylphenyl)methylene]cyclohexyl]-azetidine. GC analyses (3% SE 30) 100% at 4.99 min, UV $\lambda max(\epsilon)247(15,300)$. HR mass spectrum Found 241.1844, Calcd. for $C_{17}H_{23}N$ 241.1830. The NMR spectrum was also consistent for this named product.

EXAMPLE 8

Synthesis of the Z-isomer of 1-[2-(phenylmethylene)cyclohexyl]azetidine (Exemplifies the process of Scheme VIII.)

A. Preparation of the (E)-isomer trifluoroacetamido intermediate

To a solution of 1 g (5.3 mmol) of the E-isomer of N-[2-(phenylmethylene)cyclohexyl]amine in 20 ml of diethyl ether at 0° C., there was added 1.23 g (5.8 mmol) of trifluoroacetic anhydride over 20 min. The resulting mixture was stirred for 2 hr at room temperature. Ice was added and the pH of the mixture was adjusted to 7–8 with sodium hydroxide and stirred for 1 hr. The ether layer was washed with water and then with saturated sodium chloride solution, dried with magnesium sulfate and evaporated. The resulting crystalline solid residue, 1.4 g, was recrystallized from a diethyl ether/petroleum ether (30°–60° C. bp) mixture to obtain a crystalline solid $(\pm)$-(E)-2,2,2-trifluoro-N-[2-(phenylmethylene)cyclohexyl]acetamide, mp 109°–110° C.; GC QF-1 column 100%, retention time 4.57 min, UCW-982 column 100%, retention time 5.62 min; UV $\lambda max(\epsilon)242(14,500)$. Mass Spectrum $M+283$. The IR and NMR spectra were also consistent with this trifluoroacetamide compound, E isomer.

Anal. Calcd. for $C_{15}H_{16}F_3NO$: C, 63.59; H, 5.69; F, 20.12; N, 4.95% Found: C, 63.83; H, 5.70; F, 19.94; N, 4.99%.

B. Regeneration of 2-(phenylmethylene)cyclohexanamine, E isomer, and its monohydrochloride A mixture of the trifluoroacetamide compound from part A above, (E isomer) (1 g, 3.5 mmol), 5 ml of 20% aqueous sodium hydroxide and 5 ml of methanol was refluxed for 10 min, cooled and extracted with chloroform. The extract was washed with saturated sodium chloride solution, dried with magnesium sulfate and evaporated to leave as residue 0.63 g of the 2-(phenylmethylene)cyclohexylamine, E isomer, which was identical to a previous sample of the same compound by GC and tlc analysis comparisons.

C. Preparation of the Z isomer of 2,2,2-trifluoro-N-[N-(2-phenylmethylene)cyclohexyl]acetamide A mixture of the E and Z isomers of $(\pm)$-N-[2-(phenylmethylene)cyclohexyl]amine, 20.9 g, 0.11 mole) remaining after crystallization of the E isomer from the hydrochloric acid dehydration of the amino-alcohol, as described in Example 1, Part D, was dissolved in 400 ml of diethyl ether, cooled to 0° C., and treated during 30 min with a solution of 25.4 g, 0.12 mole of trifluoroacetic anhydride in 20 ml of the ether. The mixture was then stirred at room temperature for 3 hr and then the pH was adjusted to 6–7 with aqueous 25% sodium hydroxide solution. The ether layer was washed with water, then with saturated sodium chloride solution and dried with magnesium sulfate and evaporated. The residue, 23 g, was chromatographed using 4 kg of silica gel in a column through which was passed a 20% cyclohexane in chloroform mixture. The first 13 liters of effluent from the column gave no product. The next 2.25 liters gave 4.1 g of product which was recrystallized from petroleum ether (bp 30°–60° C.) to give the Z isomer of the sub-titled acetamide, as two crops which totaled 3.06 g, mp 122°–123° C. The analytical sample was recrystallized from a diethyl ether/petroleum ether (30°–60° C.) mixture to give crystalline Z isomer product, mp 124°–125° C. The UV, Mass spectrum and NMR spectra were consistent for this product.

Anal. Calcd for $C_{15}H_{16}F_3NO$: C, 63.59; H, 5.69; F, 20.12; N, 4.95% Found: C, 63.44; H, 5.77; F, 20.07; N, 5.09%.

D. Preparation of 2-(phenylmethylene)cyclohexylamine, Z-isomer, and its monohydrochloride A mixture of 1.4 g (5 mmole) of the 2,2,2-trifluoro-N-[2-(phenylmethylene)cyclohexyl]acetamide, Z isomer from step (c) above, 7 ml of 20% w/v aqueous sodium hydroxide solution and 7 ml of methanol was heated on a steam bath for 5 min. The methanol was evaporated and the residue was extracted with diethyl ether. The ether extract was washed with saturated sodium chloride solution, dried with magnesium sulfate and evaporated to leave 0.94 g of the N-[2-(phenylmethylene)cyclohexyl]amine, Z isomer, as a colorless oil. The NMR spectrum was consistent; the CH-N coupling pattern suggests that this H is equatorial. The GC analysis, 1% QF-1, 99.7%, retention time 2.36 min UV $\lambda max(\epsilon)243(12,000)$. The mass spectrum and IR were also consistent. The hydrochloride salt of this amine was formed in ethereal hydrogen chloride and crystallized from a methanol/diethyl ether mixture, mp 214°–215° C. The mass spectrum and IR spectrum were consistent with this sub-titled hydrochloride salt.

Anal. Calcd. for $C_{12}H_{17}N\cdot HCl$: C, 69.79; H, 8.11; Cl, 15.84; N, 6.26% Found: C, 69.75; H, 8.13; Cl, 15.86; N, 6.43%.

E. Preparation of 1-[2-(phenylmethylene)cyclohexyl]azetidine, Z-isomer

A mixture of 0.73 g (3.9 mmoles) of the 2-(phenylmethylene)cyclohexylamine, Z isomer, from step D above, 3-bromo-1-propanol (0.54 g, 3.9 mmole) and 0.54 g (3.9 mmole) of potassium carbonate in 10 ml of ethanol was stirred and refluxed for 22 hr. The resulting mixture was evaporated and the residue was taken up in a diethyl ether/water mixture. The ether layer extract was separated and washed with saturated sodium chloride solution, dried with magnesium sulfate and evaporated. The residue was chromatographed on a HPLC apparatus, using Merck, size C, silica gel column and a 1% v/v methanol in chloroform mixture containing 0.25% v/v ammonium hydroxide to get the residue on the column. Elution of the column with a 2% v/v methanol in chloroform mixture containing 0.25% ammonium hydroxide gave 0.25 g of product. NMR and mass spectrum analysis of this product indicated a mixture of the -amine starting material and -azetidine product. This mixture, 0.21 g, was dissolved in 5 ml of diethyl ether, cooled to 0° C. and treated with a solution of 0.24 g of trifluoroacetic anhydride in 5 ml of diethyl ether. After stirring for 30 min, the pH was adjusted to 7–8 and the mixture was extracted with diethyl ether. The ether solution was extracted with three 5 ml portions of 5% acetic acid. The acid layer was separated and cooled (saved the neutral layer), basified and then saturated with diethyl ether, dried with magnesium sulfate and evaporated to leave 49 mg of the 1-[2-(phenylmethylene)cyclohexyl]azetidine, Z isomer as an oil, IV $\lambda max(\epsilon)239.5(10,200)$. Mass spectrum found M.W. 227.1670; theory for $C_{16}H_{21}N$ 227.1674. The NMR was also consistent with this named compound isomer. The above neutral layer was worked up to give 155 mg of crystalline solid. A mixed melting point determination of this crystalline material with authentic (±)-(Z)-2,2,2-trifluoro-N-[2-phenylmethylene)cyclohexyl]amine showed no depression. The above step E reaction was also run using 1,3-dibromopropane (4 equivalents) in place of 3-bromo-1-propanol to give 25% yield of the 1-[2-(phenylmethylene)cyclohexyl]azetidine accompanied by N,N-diallyl- and N-allyl-N-[2-(phenylmethylene)cyclohexyl]amine, which were separated by chromatography.

EXAMPLE 9

1-[2-[[4-(trifluoromethyl)phenyl]methylene]cyclohexyl]azetidine (Exemplifies the process of Scheme IX.)

A. Preparation of 1-[2-[[4-(trifluoromethyl)phenyl])(hydroxy)methyl]cyclohexyl]azetidine A mixture of 2-[4-(trifluoromethyl)benzoyl]cyclohexanone, 5.4 g, 0.02 mole, with 2.28 g, 0.04 mole of azetidine and 25 mg of p-toluenesulfonic acid in 50 ml of benzene was refluxed for 17 hr using a Soxhlet device containing 50 g of 3A molecular sieves. The resulting solution was evaporated, the residue was dissolved in 75 ml of ethanol and hydrogenated in the presence of 0.5 g of platinum dioxide ($PtO_2$) at an initial pressure of 54 psig for 1.5 hr. The mixture was filtered, cooled in ice and treated with 5.4 g of sodium borohydride ($NaBH_4$) and stirred at room temperature for 16 hr. The mixture was then evaporated, the residue taken up in a water/diethyl ether mixture, the ether extract being separated and washed with saturated sodium chloride solution, dried with magnesium sulfate and evaporated. Trituration of the residue with diethyl ether gave 0.76 g (plus filtrate) of the N-[2-[[4-(trifluoromethyl)phenyl](hydroxy)methyl]cyclohexyl]azetidine as a colorless solid, mp 163°–165° C., which was raised to 167°–168° C. on recrystallization from methanol. The UV $\lambda max(\epsilon)216(9,550)$, 252(382), 258(442), 263(411), 258(307). The IR and Mass spectral analyses were consistent. The NMR ($CDCl_3$) indicated that the product contained a mixture of two diastereoisomers. $\delta 7.6$–7.4(m,5H,aromatic) 5.1(m,1H, HC—O), 2.7(m,1H, CH—N), 2.2–1.9(m,3H, CH—C—O and C—CH$_2$—C of azetidine), 1.9–0.9(m,8H, CH$_2$'s).

Anal. Calcd for $C_{17}H_{22}F_3NO$: C, 65.15; H, 7.08; F, 18.19; N, 4.47% Found: C, 65.37; H, 7.20; F, 18.02; N, 4.32%.

Chromatography of the above filtrate on silica gel using a 5% methanol v/v in chloroform containing 0.5% ammonium hydroxide mixture as eluting solvent afforded an additional 0.366 g of the 1-[2-[[4-(trifluoromethyl)phenyl](hydroxy)methyl]cyclohexyl]azetidine.

B. Preparation of 1-[2-[[4-(trifluoromethyl)phenyl]methylene]cyclohexyl]azetidine A 0.4 g (1.3 mmole) portion of 1-[2-[[4-(trifluoromethyl)phenyl](hydroxy)methyl]cyclohexyl]azetidine, from step A above was added during 5 min to 4 ml of ice cooled sulfuric acid. The mixture was stirred in ice for 20 min. The resulting mixture was poured into ice, basified with sodium hydroxide, and extracted with six 30 ml portions of chloroform. The chloroform extracts were combined and dried with magnesium sulfate and evaporated to give 0.173 g of (±)-(E)-1-[2-[[4-(trifluoromethyl)phenyl]methylene]cyclohexyl]azetidine. The crystalline p-toluenesulfonic acid salt of this azetidine derivative was prepared, mp 135°–136° C. UV $\lambda max(\epsilon)219sh(17,350)$ 222(17,400) 227sh(15,250) 246(11,750)IR,NH $R_f$ 3000b, 2600, 1660 C=C, 1615, 1575, 1495, 1325 $SO_3/CF_3$, 1230, 1215, 1175, 1125, 1065, 1035, 1010, 814 aromatic, 805, 680. NMR ($d_6$DMSO)$\delta 7.75$,7.1(2d,4H,aromatic of TSA), 7.6–7.4 (m,4H,aromatic), 4.1–3.8(m,5H,—CH—N(CH$_2$)—CH$_2$ move upfield with addition of NaOH, 2.6–211 (m,4H,CH$_2$—C=C+C—CH$_2$— of azetidine), 2.3 (s,3H,CH$_3$), 1.9–1.45(m,6H,CH$_2$'s).

EXAMPLE 10

1-2-[[4-[(4-methylphenyl)methoxy]phenyl]methylene] cyclohexyl]azetidine

A. Preparation of 2-[[4-[(4-methylphenyl)methoxy]phenyl](hydroxy)methyl]cyclohexanone A mixture of diisopropylamine (19.9 ml., 0.14 mol) and 150 ml of tetrahydrofuran under Argon gas was cooled to −20° C. and n-butyllithium (80 ml of 1.55M in hexane, 0.12 mol) was added over 0.16 hr and cooled to −78° C. Cyclohexanone (12.07 g, 0.123 mol) in tetrahydrofuran (100 ml) was added over 0.15 hr. A solution of 25.3 g (0.11 mol) of 4-(4-methylbenzyloxy)benzaldehyde in 150 ml of degassed tetrahydrofuran was added in 5 seconds at −78° C. and stirred at that temperature for 4 minutes. Then 150 ml of saturated ammonium chloride aqueous solution was added and the resulting mixture was removed from the cold bath. After warming to room temperature, the liquid layers were separated and the aqueous layer was extracted with diethyl ether. The organic liquid layer and ether extract were combined and washed twice with saturated sodium chloride solution and dried with magnesium sulfate. The solvent was removed under vacuum to give 44.29 g of a yellow semi-solid which was boiled with Skellysolve B and decanted from an insoluble yellow solid. The solution was decanted twice more while cooling and finally cooled in an ice bath to give 14.88 g (41% yield) of a slightly yellow solid which is a mixture of the erythro and threo sub-titled aldol products. The precipitate which remained after decanting was boiled with another 250 ml of Skellysolve B and decanted. The solution was decanted once while cooling and finally cooled in an ice bath to give 3.84 g of a slightly yellow solid. Purification by medium pressure liquid chromatography procedures (50 psig, Silica gel, 40–63 μm, 47×450 mm Michel-Miller column, 24 ml/min; 4:1 v/v cyclohexane/ethyl acetate) gave two major bands.

Band 1: $R_f$=0.28, 1.14 g. Recrystallization from cyclohexane gave colorless needle crystals, mp 115.5° C. NMR (Dueterated chloroformtetramethylsilane)δ 1.3–2.0 (m, 6H, cyclohexyl $CH_2$), 2.0–2.75 (m, 3H, $CH_2C(O)CH$), 2.35 (s, 3H, $CH_3$), 2.95 (d, J=3.6 Hz, 1H, exch. OH), 5.00 (s, 2H, $OCH_2$), 5.28 (dd, 1H, CHOH), 7.08 ($A_2B_2$, 4, Phenyl H), 7.24 ($A_2B_2$, 4, Phenyl H).

When exchanged with $D_2O$ the dd at 5.28 collapses to a doublet, J=2.6 Hz which suggests this is the erythro adduct. IR: OH 3476, C=O 1700. UV (Ethanol) λ max (ε) 212 sh (17,400), 224 (20,350), 269 sh (1550), 274 (1750), 281 (1350); Mass Spectrum M+ at m/e 324.

Anal. Calcd. for $C_{21}H_{24}O_3$: C, 77.75; H, 7.46. Found: C, 77.57; H, 7.45.

Band 2: $R_f$=0.19, 1.54 g. Recrystallization from cyclohexane gave colorless needle crystals (mp 120° C.). NMR (CDCl$_3$-TMS) δ 1.0–1.9 (m, 6H, cyclohexyl $C_2$), 1.9–2.8 (m, 3, $CH_2$—C(O)CH), 2.35 s, 3, $CH_3$), 3.89 (d, J=2.8 Hz, 1H, OH, exch.), 4.73 (dd, 1H, collapses to d with $D_2O$, J=8.8 Hz, CHOH, threo), IR; OH 3507, C=O 1688. UV (ethanol) λ max (ε) 212 sh (16,600), 224 (20,400), 269 sh (1450), 274 (1700), 281 (1350), 320 sh (143); Mass spectrum M+ m/e 324.

Anal. Calcd. for $C_{21}H_{24}O_3$: C, 77.75; H, 7.46. Found: C, 77.44; H, 7.48.

B. Preparation of 2-[[4-[(4-methylphenyl)methoxy]phenyl]methylene]cyclohexanone

The hydroxymethylcyclohexanone, 14.8 g, 0.0475 mol. as a mixture of diastereomers, from Step (A) above, and 16 ml (0.12 mole) of triethylamine was dissolved in 225 ml of tetrahydrofuran and the solution was cooled to 0° C. Methanesulfonyl chloride was added dropwise over 0.2 hr and the solution was stirred at 0° C. for 0.6 hr. Then 7.7 ml (0.062 mol) of 1,5-diazabicyclo[4.3.0]non-5-ene (DBN) was added in one shot and the resulting mixture was stirred at 0° C. for 0.7 hr and then at room temperature for 1.3 hr. The mixture was then diluted with diethyl ether and washed with water, three times with 100 ml portions of 10% hydrochloric acid solution, twice with 100 ml portions of saturated sodium bicarbonate solution, then with saturated sodium chloride solution and dried with magnesium sulfate. The solvent was removed in vacuo to leave as residue 14.7 g of a yellow solid. Recrystallization from cyclohexane gave 12.3 g (88% yield) of the sub-titled 2-(phenylmethylene)cyclohexanone as a yellow solid which contained impurities but which was used as an intermediate without further purification.

The filtrate was evaporated to dryness (2.74 g of residue) and this was combined with 0.47 g of recrystallized material. The mixture was stirred with methylene chloride and filtered to remove an insoluble yellow solid. The filtrate was concentrated to 15 ml and purified via low pressure chromatography (Silicon dioxide, 0.04–0.063 mm, 47×450 mm Michel-Miller column, at a rate of 24 ml/min) eluting with a 4:1 v/v (500 ml) and a 9:1 v/v (1000 ml) of methylene chloride/cyclohexane mixtures, and then with pure methylene chloride to give 1.35 g of a slightly yellow solid. Recrystallization from ethanol gave tan needle crystals of 2-[[4-(4-methylbenzyloxy)phenyl]methylene]cyclohexanone, mp 147.5°–149° C. NMR: (CDCl$_3$-TMS) δ 1.5–2.1 (m, 4H, cyclohexyl $CH_2$), 2.35 (s, 3H, $CH_3$), 2.51 (t, J=6 Hz, 2H, —C(O)$CH_2$), 2.78 (br. t, 2H, C=C—$CH_2$), 5.03 (s, 2H, $OCH_2$), 7.16 ($A_2B_2$, 4H, phenyl H), 7.24 ($A_2B_2$, 4H, phenyl H), 7.46 m, 1H, C=C—H—.

Reaction of the substituted phenylmethylenecyclohexanone with ammonium acetate and sodium cyanoborohydride produced the corresponding cyclohexylamine, which amine was then reacted with 1,3-dibromopropane, as described above, to give the 1-[2-[[(4-methylbenzyloxy)phenyl]methylene]cyclohexyl]azetidine, which was recrystallized from methanol to give a crystalline product, mp 88°–90° C.

Anal. Calcd. for $C_{24}H_{29}NO$: C, 82.95; H, 8.41; N, 4.03. Found: C, 82.98; H, 8.44; N, 3.95. Mass Spectrum: Calcd. 347.2249; Found 347.2253.

EXAMPLE 11

(+)-(E)-1-[2-(phenylmethylene)cyclohexyl]azetidine, maleate salt and (−)-(E)-1-[2-(phenylmethylene)cyclohexyl]azetidine maleate salt Racemic (E)-1-[2-(phenylmethylene)cyclohexyl]azetidine (11.37 g, 0.05 mole), (obtained from the maleate by basification) and dibenzoyl-d-tartaric acid monohydrate (18.8 g, 0.05 mole) were dissolved in 75 ml of methanol and 400 ml of diethyl ether and allowed to crystallize overnight. The crystalline material was collected by filtration (this filtration mother liquid was saved for recovery of the other titled enantiomer as described below). The solid was recrystallized three more times to constant rotation to give 10.8 g of the diastereomeric (−)-isomer of the tartrate salt, which had mp 164°–165° C., mass spectrum m/e M+ 227, [α]$_D$−46° (8.57 mg/ml in methanol), and nmr, ir, and UV spectra consistent with the structure.

Anal. Calcd. for $C_{16}H_{21}NC_{18}H_{14}O_8$: C, 69.72; H, 6.02; N, 2.39; Found: C, 69.67; H, 6.01; N, 2.38.

The 1-[2-(phenylmethylene)cyclohexyl]azetidine free base was released from this (−)-tartrate salt. This resulting (+)-isomer of the titled free base was converted to the maleate salt which had a mp 115°–116° C. and [α]$_D$= +54° (5.12 mg/ml in methanol) and nmr, ir, and UV spectra identical to those of the racemate.

Anal. Calcd. for $C_{16}H_{21}NC_4H_4O_4$: C, 69.95; H, 7.34; N, 4.08; Found: C, 69.91; H, 7.65; N, 3.78.

The mother liquor saved from the original recrystallization as described above was concentrated, basified, and extracted with ether. The recovered amine (5.22 g, 0.023 mole) and dibenzoyl-1-tartaric acid monohydrate (8.66 g, 0.023 mole) were dissolved in 75 ml of methanol and 400 ml of diethyl ether and allowed to crystallize overnight (about 16 hours). The crystalline material was collected by filtration and recrystallized twice more to constant rotation to give 10.0 g of the diastereomeric (+)-isomer of the tartrate salt, which had mp 164°–165° C., $[\alpha]_D = +47°$ (5.05 mg/ml in methanol) and nmr, ir, UV, and mass spectra identical to those of the above-tartrate salt.

Anal. Found for $C_{16}H_{21}NC_{18}H_{14}O_8$: C, 69.82; H, 5.97; N, 2.10.

The titled levo (−)-isomer was released from this (+)-tartrate salt and converted to the maleate salt as above. This titled (−)-isomer maleate salt showed mp 115°–116° C., $[\alpha]_D = -53°$ (4.50 mg/ml in methanol), and nmr, ir, UV, and mass spectra identical to those of the racemate.

Anal. Found for $C_{16}H_{21}NC_4H_4O_4$: C, 69.67; H, 7.33; N, 3.99.

EXAMPLE 12

1-[2-(phenylmethylene)cyclohexyl]azetidine
(Exemplifies part of the process of Scheme VI.)

A. 2-(phenylmethylene)cyclohexanone

According to the procedure of Birkofer, et al., *Chem. Ber.*, 85, 1495 (1962), a mixture of 1-morpholinyl-1-cyclohexene (125.2 g. 0.75 mole), prepared as described above, benzaldehyde (53.1 g, 0.5 mole), and 200 ml of benzene was refluxed for 12 hours with azeotropic separation of 5.3 ml of water. The reaction mixture was cooled and treated with 300 ml of 6N aqueous hydrochloric acid and stirred at room temperature for one hour. The organic layer was separated, the aqueous layer was extracted with diethyl ether, and the combined organic layer was washed with saturated aqueous sodium chloride solution, dried (MgSO$_4$), and concentrated. Distillation in vacuo (0.07 mm Hg) gave a fraction bp 124°–128° C., 61.1 g of the subtitled product (96.2% pure by gas liquid chromatography (GLC) gas analysis). Crystallization from diethyl ether—petroleum ether (30°–60° C.) at −70° C. gave 47.7 g of the subtitled product, mp 48°–50° C. (100% pure by GLC; Birkhofer, et al., loc cit report mp 56° C.

B. 2-(phenylmethylene)cyclohexylamine

Molecular sieve (size 3A, 2 g) was added to a solution of 2-(phenylmethylene)cyclohexanone (1.86 g, 0.01 mole) in 20 ml of methanol, followed by a solution of ammonium acetate (7.7 g, 0.1 mole) in 20 ml of methanol. The mixture was cooled to about 10° C., and a solution of sodium cyanoborohydride in 20 ml of methanol was added during five minutes. The mixture was stirred at ambient temperature for 19 hours. The mixture was filtered, and the filtrate was cooled and brought to pH 11 by the addition of 20% aqueous sodium hydroxide. The methanol was evaporated and the mixture was extracted with ether. The extract was washed with water (water layer discarded) and then with three 10 ml portions of 10% aqueous hydrochloric acid. Water was added to dissolve the resulting solid. The aqueous acidic layer was cooled, basified with sodium hydroxide and extracted with chloroform. The chloroform extract was washed with water and saturated sodium chloride solution, dried over anhydrous magnesium sulfate and evaporated to give 1.2 g of (±)-(E)-2-(phenylmethylene)cyclohexylamine which was identical (by tlc, UV, and nmr comparison) to the amine prepared in Part D of Example 1 above.

If desired this amine can be converted to an azetidine compound of this invention by procedures described herein.

An alternative and more recently used process for making the above 2-(phenylmethylene)cyclohexylamine starts with E-2-benzylidenecyclohexanone, which is made from benzaldehyde and cyclohexanone via an aldol condensation procedure, which follows generally literature procedures disclosed by H. M. Walton, *J. Org. Chem.*, 22, 1161 (1957) and A. T. Nielson et al., *Org. Reactions*, 16, 1 (1968), and then conversion of the resulting (E)-2-(benzylidene)cyclohexanone to the desired 2-(phenylmethylene)cyclohexylamine by a modification of the above procedure, described herebelow.

(E)-2-(benzylidene)cyclohexanone

Into an inert 100 gallon reactor, there is drawn 29.3 kg of cyclohexanone from a grounded drum on a weight scale. The reactor is vented with nitrogen and then 28.5 kg of benzaldehyde is added. Then 125 liters of deionized water is metered into the above mixture. The vessel is closed and 'reinserted' with nitrogen. To the resulting reactor contents there is added, from a grounded drum on a weight scale, a 50 percent (w/v) solution of sodium hydroxide in water solution, (10.6 kg), while stirring the mixture. The resulting mixture is stirred and heated to reflux (about 98° C.) under an atmosphere of nitrogen. The mixture is held at reflux temperature for about three hours and then stirred and cooled overnight. The resulting cooled reaction mixture is extracted once with a 198 liter batch of methylene chloride, separating the aqueous layer, and then again with 132 liters of methylene chloride, neutralizing and discarding the aqueous layer. The combined methylene chloride liquid layers are washed with 284 liters of water and then with 284 liters of water containing 50 ml of acetic acid. After aqueous layer separation, the methylene chloride liquid layer is dried over sodium sulfate with stirring. The resulting dried methylene chloride layer is concentrated to an oil using 35° C. jacket water temperature and jet vacuum procedures. The (E)-2-(benzylidene)cyclohexanone is crystallized by dissolving the oily residue in 60 liters of Skellysolve ® B and seeding with authentic material and cooling the vessel overnight by circulating a cooled water/methanol mixture through the reactor jacket. The pale yellow crystals are collected on a 24-inch filter, washed with Skellysolve ® B, and recrystallized from 75 gallons of Skellysolve ® B by heating to 50° C. to effect dissolution and then cooling the tank contents to 0° C. Alternatively, we have used isopropanol in this crystallization step with approximately equal effectiveness in terms of quality of the crystalline intermediate (E)-2-(benzylidene)cyclohexanone. The crystalline intermediate is dried in a vacuum oven at room temperature to give about 16.4 kg (33 percent yield) of the (E)-2-(benzylidene)cyclohexanone, m.p. 47°–54° C. (Lit. m.p. 54° C.). TLC analysis (silica gel GF; 5 percent ethyl acetate in Skellysolve ® B developer) indicates the presence of a small amount of a less polar impurity, identified as

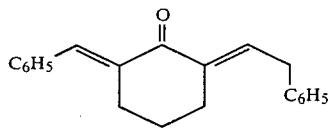

on the basis of isolation and melting point.

Concentration of the filtrate from the recrystallization step to a small volume, followed by cooling to 0° C. gives a second crop of (E)-2-(benzylidene)cyclohexanone, 4.3 kg (9 percent), m.p. 38°–47° C.

2-(Phenylmethylene)cyclohexylamine

To a dried, 100 gallon, inert reactor vessel there is added about 8.4 kg of the (E)-2-(benzylidene)cyclohexanone, prepared as described above. The vessel cover is secured, the vessel is reinerted, and then 72 kg (24 gallons) of methanol are added to the reactor from a grounded drum. To a 50 gallon open top tank in a walk-in hood there is added 34.85 kg of ammonium acetate crystal. Methanol, 24 gallons, 72 kg, is the blown in to the open top tank from a grounded drum. Then 8 liters of distilled water is added. The mixture is stirred to dissolve the crystalline material, and then the resulting solution is transferred to the reactor vessel. The resulting mixture in the reactor vessel is cooled to about +10° C. and the coolant is allowed to remain in the reactor jacket. Using appropriate respirator and glove safety protection, about 2.0 kg of sodium cyanoborohydride is added to the empty open top tank used above. Then 24 gallons, 72 kg. of methanol is added from a grounded drum and the mixture is stirred to effect dissolution. The resulting solution is transferred from the open-top tank to the reactor vessel. The reactor vessel contents are stirred while a brine filled (water/methanol mixture) jacket is turned off until TLC analysis (silica gel GF, using 5 percent ethyl acetate is hexane developer and UV and iodine visualization) indicates the reaction is complete. The reactor contents are then cooled to +5° C. using cooled methanol coolant in the jacket. Then the pH of the reaction mixture is cautiously raised to 10 or above by adding 30.9 kg potassium hydroxide pellelt, or equivalent, in portions with good stirring. Ammonia is liberated from the reactor vessel.

The methanol solvent is distilled using a jet vacuum and 35°–40° C. water in the reactor jacket. The residue is then treated with 40 gallons of saturated aqueous sodium chloride, while cold water is running through the reactor jacket. The aqueous mixture in the reactor vessel is extracted once with 30 gallons of ethyl ether and then three times with twelve gallon portions of ethyl ether. The combined ethyl ether fractions are washed with 10 gallons of saturated sodium chloride solution. The combined ether extracts, after separation from the last aqueous phase, is dried over anhydrous potassium carbonate while stirring. The dried ether phase is filtered and the ethyl ether is removed under vacuum pressure from the filtrate to leave as residue an orange oil. The oil is dissolved in 5 gallons of methylene chloride. The resulting methylene chloride solution is passed through a 12-inch stainless steel chromatography column containing 175 kg of silica gel, eluting the column and the product with a 5 percent (v/v) methanol in methylene chloride mixture.

The eluting fractions are taken in two 50 gallon fractions and then with 30 gallon fractions thereafter. Fractions containing the desired, essentially pure 2-(phenylmethylene)cyclohexylamine as determined by TLC analysis (silica gel GF; 5 percent methanol in methylene chloride containing 4 drops of concentrated ammonium hydroxide per 20 ml of solution and UV and iodine visualization) are combined. Fractions 6 to 17 are combined to afford 4832 g (57 percent yield) of 2-(phenylmethylene)cyclohexylamine which partially crystallized on standing. Crystallization of this amine product is completed by trituration with hexane. A total of 4.2 kg of crystalline 2-(phenylmethylene)cyclohexylamine is obtained after drying in vacuo at 23° C.

Analysis Calcd. for $C_{13}H_{17}N$: C, 83.37; H, 9.15; N, 7.48% Found: C, 82.74; N, 9.02; N, 7.28%

Equivalent Weight: Calcd: 187; Found: 189.

Melting Point 44°–50° C.

Material of this purity is suitable for use in making the azetidine or other amine products, referred to above, in fewer overall reaction steps.

This invention also relates to compositions containing a formula I compound as an active ingredient in a pharmaceutical carrier. The compositions are useful in pharmaceutical dosage unit forms of the formula I compounds for local (topical) and systemic administration (oral, rectal and parenteral administration form) in therapy for treating and alleviating pain in humans and valuable animals, including dogs, cats and other commercially valuable and domestic animals.

The term "dosage unit form" as used in this specification and in the claims refers to physically discrete units suitable as unitary dosages for mammalian subjects, each unit containing a predetermined quantity of the essential active ingredient compound of this invention calculated to produce the desired effect, in combination with the required pharmaceutical means which adapt the said ingredient for systemic administration. The specification for the novel dosage unit forms of this invention are dictated by and directly dependent on the physical characteristics of the essential active ingredient and the particular effect to be achieved in view of the limitations inherent in the art of compounding such an essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, lactose, kaolin, dicalcium phosphate, gelatin, acacia, corn syrup, corn starch, talc and the like. Capsules, both hard and soft, are filled with compositions of the selected formula I compound or salt thereof ingredients in combination with suitable diluents and excipients, for example, edible oils, talc, calcium carbonate and the like and also calcium stearate. Liquid preparations for oral administration are prepared in water or aqueous vehicles which advantageously contain suspending agents, for example, methylcellulose, acacia, polyvinylpyrrolidone, polyvinyl alcohol and the like. In the case of injectable forms, the injectable formulation must be sterile and must be fluid to the extent that easy syringeability exists. Such preparations must be stable under the conditions of manufacture and storage, and ordinarily contain in addition to the basic solvent or suspending liquid, preservatives in the nature of bacteriostatic and fungistatic agents, for example, parabens, chlorobutanol, benzyl alcohol, phenol, thimerosal, and the like. In many cases, it is preferable to include osmotically active agents, for example, sugars or sodium chloride in isotonic concentrations. Carriers and vehicles include vegetable oils, ethanol, polyols, for example, glycerol, propylene glycol, liquid polyethylene glycol, and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 0.5 to about 350 mg of the essential active ingredient per dosage unit form, which as aforesaid may be in the form of a semi-solid or solid oral preparation, or a liquid oral preparation. The amount of the essential active formula I compound, or pharmaceutically acceptable salt thereof, ingredient provided in the pharmaceutical dosage unit forms is that amount sufficient to obtain analgesic and/or antidepressant effects within the aforesaid effective non-toxic range. Expressed otherwise, when used systemically, an amount of the essential active ingredient is provided to a recipient within a range from about 0.01 mg/kg to about 5 mg/kg of body weight of the recipient. Preferred dosages for most applications are 0.05 to 2.0 mg/kg of body weight.

The useful pharmaceutical dosage unit forms of these compounds in pharmaceutical formulations is preferably adapted for oral administration to obtain analgesic and/or antidepressant effects comprising an effective, non-toxic amount of a compound according to formula I or as its pharmacologically acceptable salt.

Further the invention relates to methods of obtaining analgesic and/or antidepressant effects in mammals, for example, human and valuable warm-blooded animals such as dogs, cats, horses and other commercially valuable animals, by administering systemically to the mammals the aforesaid formula I compound or pharmaceutically acceptable salt thereof in pharmaceutical dosage unit forms supplying an effective, non-toxic amount of such compound for analgesic and/or antidepressant effects.

The lead compound ($\pm$)-(E)-1-[2-(phenylmethylene)cyclohexyl]azetidine has an advantage of having no physical dependence liability in contrast to known analgesic compounds such as morphine and methadone, as shown by evaluation of this compound and those standard analgesic drug compounds in various pharmacological test procedures which measure relative degrees of analgesia and the physical dependence liability of the test compounds in standard laboratory test animals.

The compound ($\pm$)-(E)-1-[2-(phenylmethylene)cyclohexyl]azetidine has several biological actions in common with nefopam (3,4,5,6-tetrahydro-5-methyl-1-phenyl-1H-2,5-benzoxazocine; and MERCK INDEX 9th Edition, (1976), page 837), a non-opioid centrally acting analgesic. Compared to nefopam, ($\pm$)-(E)-1-[2-(phenylmethylene)cyclohexyl]azetidine has an analgesic potency 1 to 10 times greater in animal tests and a therapeutic ratio 5 to 50 times better.

Animal studies also reveal that ($\pm$)-(E)-1-[2-(phenylmethylene)cyclohexyl]azetidine potentiates yohimbine and apomorphine, blocks oxotremorine, and blocks uptake of serotonin or norepinephrine, in standard laboratory animal tests. However, it did not inhibit monoamine oxidase and it did not displace serotonin in rat brain homogenates. The similarities of these properties of ($\pm$)-(E)-1-[2-(phenylmethylene)cyclohexyl]azetidine to properties of tricyclic antidepressants, such as imipramine and amitriptyline, and the lack of tolerance suggests that ($\pm$)-(E)-1-[2-(phenylmethylene)cyclohexyl]azetidine will be especially useful for treating chronic pain conditions, because patients suffering chronic pain often have the concomitant problem—depression. Depression is commonly associated with enduring pain. Whether the depression condition precedes the pain or results from it, the depression presents an additional element of suffering, which hopefully can be alleviated by an analgesic with antidepressant properties, such as the presently provided ($\pm$)-(E)-1-[2-(phenylmethylene)cyclohexyl]azetidine.

($\pm$)-(E)-1-[2-(phenylmethylene)cyclohexyl]azetidine and other formula I compounds of this invention should have relatively low abuse potential.

Although ($\pm$)-(E)-1-[2-(phenylmethylene)cyclohexyl]azetidine is not as effective acutely to alleviate pain in animal tests as are the opiates, ($\pm$)-(E)-1-[2-(phenylmethylene)cyclohexyl]azetidine has the advantage in chronic use as opiate analgesics become less effective. Thus, ($\pm$)-(E)-1-[2-(phenylmethylene)cyclohexyl]azetidine will be useful in a wide range of clinical situations, for treating both acute and chronic moderate and mild pain, and chronically as a replacement analgesic drug when opiate analgesics no longer control strong pain.

Also, sedation, a common side effect for known analgesics effective against moderate pain, interferes with the patient's ability to work. The compound of this invention, ($\pm$)-(E)-1-[2-(phenylmethylene)cyclohexyl]azetidine, is unlikely to cause sedation. In standard laboratory animal tests this compound did not antagonize bicucullininduced convulsions nor potentiate gamma butyrolactone sleep. Thus, it is hoped that in clinical trials with humans ($\pm$)-(E)-1-[2-(phenylmethylene)cyclohexyl]azetidine will provide good analgesic and antidepressant properties with little if any sedation.

EXAMPLE 13

One thousand tablets for oral use, each containing 40 mg of ($\pm$)-(E)-1-[2-(phenylmethylene)cyclohexyl]azetidine succinate as the essential active ingredient are prepared from the following ingredients

| | |
|---|---|
| Essential active ingredient | 40 gm |
| Dicalcium phosphate | 150 gm |
| Methylcellulose, USP (15 cps) | 6.5 gm |
| Talc | 20 gm |
| Calcium stearate | 2.0 gm |

The essential active ingredient and dicalcium phosphate are mixed well, granulated with 7.5% aqueous solution of methylcellulose, passed through a No. 8 screen and dried carefully. The dried granules are passed through a No. 12 screen, mixed with the talc and stearate and compressed into tablets. These tablets are useful in the treatment of low back pain in adult humans at a dose of 1 tablet 1–4 times a day as needed.

EXAMPLE 14

One thousand two-piece hard gelatin capsules for oral use, each capsule containing 20 mg of (±)-(E)-1-[2-(phenylmethylene)cyclohexyl]azetidine succinate as the essential active ingredient are prepared from the following ingredients:

| Essential active ingredient | 20 gm |
|---|---|
| Lactose, USP | 100 gm |
| Starch, USP | 10 gm |
| Talc, USP | 5 gm |
| Calcium stearate | 1 gm |

The finely powdered materials are mixed thoroughly, then filled into hard gelatin capsules of appropriate size.

One capsule 4 times daily is useful for the treatment of dental pain in adult humans.

EXAMPLE 15

One-piece soft elastic capsules for oral use, each containing 100 mg of (±)-(E)-1-[2-(phenylmethylene)cyclohexyl]azetidine succinate as the essential active ingredient are prepared in the usual manner by first dispersing the active material in sufficient corn oil to render the material capsulatable.

One capsule two times daily is useful in the treatment of pain in adult humans.

EXAMPLE 16

An aqueous oral preparation containing in each teaspoonful (5 ml) 80 mg of (±)-(E)-1-[2-(phenylmethylene)cyclohexyl]azetidine succinate as the essential active ingredient is prepared fom the following ingredients:

| Essential active ingredient | 160 gm |
|---|---|
| Methylparaben, USP | 7.5 gm |
| Propylparaben, USP | 2.5 gm |
| Saccharin | 12.5 gm |
| Glycerine | 3000 ml |
| Tragacanth powder | 10 gm |
| Orange oil flavor | 10 gm |
| Orange II | 7.5 gm |
| Deionized water, q.s. to | 10000 ml |

The foregoing aqueous preparation is useful in the treatment of adult pain due to muscle spasm at a dose of 1 teaspoonful 4 times daily.

EXAMPLE 17

One thousand tablets for oral administration, each containing 10 mg of (±)-(E)-1-[2-(phenylmethylene)cyclohexyl]azetidine succinate as the essential active ingredient are prepared from the following ingredients:

| Essential active ingredient, micronized | 10 gm |
|---|---|
| Lactose | 150 gm |
| Starch | 15 gm |
| Magnesium stearate | 1.5 gm |

The ingredients are thoroughly mixed and slugged. The slugs are broken down by forcing through a screen and the resulting granules are then compressed into tablets.

These tablets are useful in reducing post-surgical pain in dogs at a dose of 1–3 tablets depending on the weight of the animal and its condition.

EXAMPLE 18

A sterile aqueous suspension suitable for intramuscular injection and containing in each milliliter 50 mg of (±)-(E)-1-[2-(phenylmethylene)cyclohexyl]azetidine succinate as the essential active ingredient is prepared from the following ingredients:

| Essential active ingredient | 5 gm |
|---|---|
| Polyethylene glycol 4000, USP | 3 gm |
| Sodium chloride | 0.9 gm |
| Polysorbate 80, USP | 0.4 gm |
| Sodium metabisulfite | 0.1 gm |
| Methylparaben, USP | 0.18 gm |
| Propylparaben, USP | 0.02 gm |
| Water for injection, q.s. to | 100 ml |

The preceding sterile injectable is useful in the treatment of pain at a dose of one-half to 2 ml.

FORMULAS

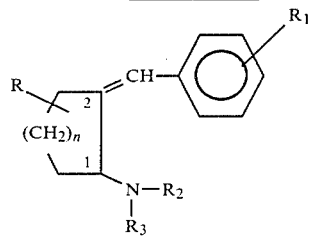

I

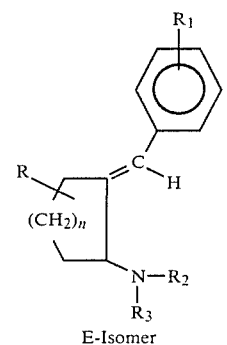

Ia

E-Isomer

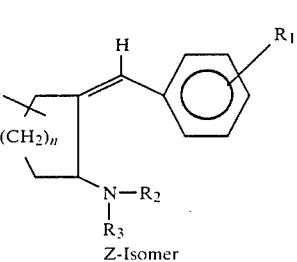

Ib

Z-Isomer

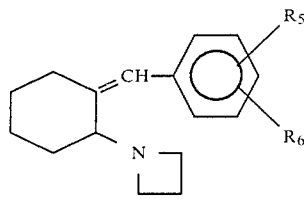

(II)

-continued
FORMULAS

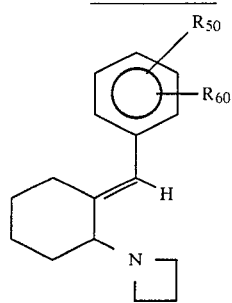 (III)

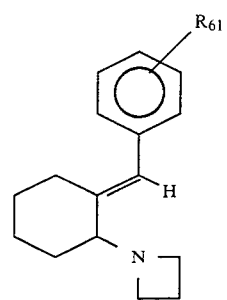 (IV)

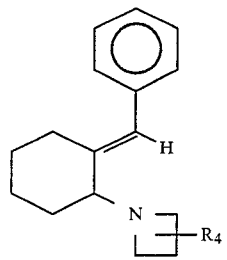 (V)

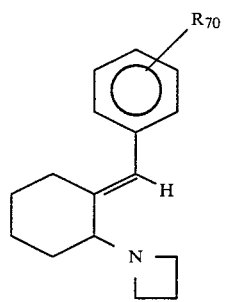 (VI)

SCHEME I
PROCESS - AZETIDINES VIA
HYDROXYPROPYL AMINES

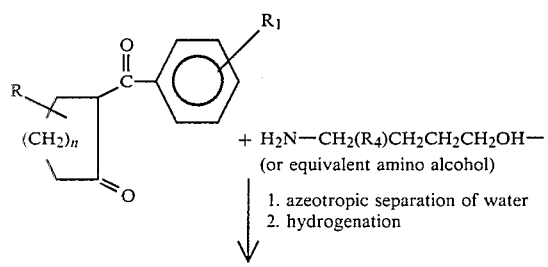

+ $H_2N-CH_2(R_4)CH_2CH_2CH_2OH$ →
(or equivalent amino alcohol)

1. azeotropic separation of water
2. hydrogenation

-continued
SCHEME I
PROCESS - AZETIDINES VIA
HYDROXYPROPYL AMINES

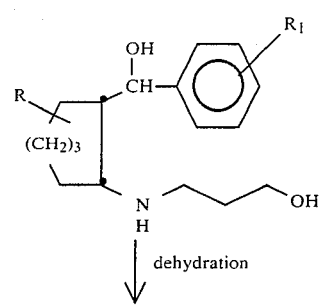

↓ dehydration

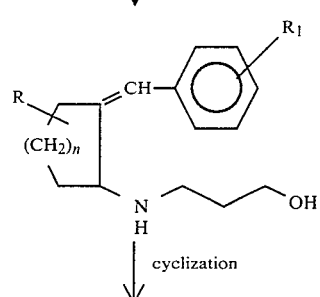

↓ cyclization

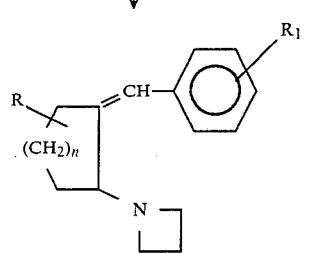

SCHEME II
PROCESS-AZETIDINES VIA SULFONATED
INTERMEDIATES

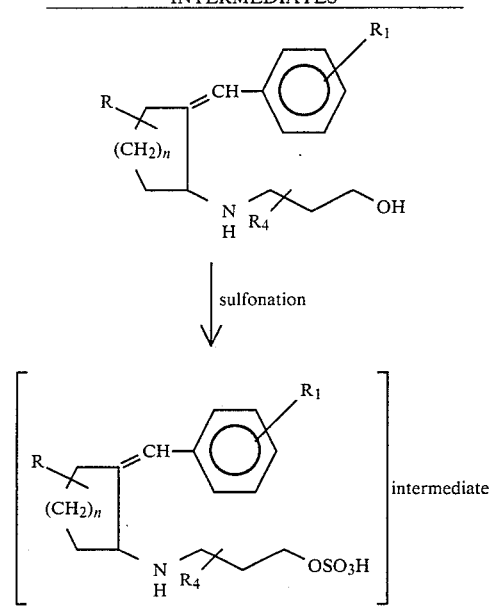

↓ sulfonation

] intermediate

-continued
SCHEME II
PROCESS-AZETIDINES VIA SULFONATED
INTERMEDIATES
↓ base, heat
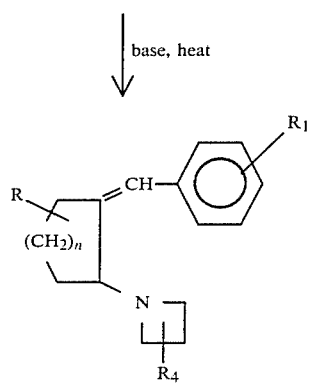
Scheme III
PROCESS-DE-ETHERIFICATION OPTION
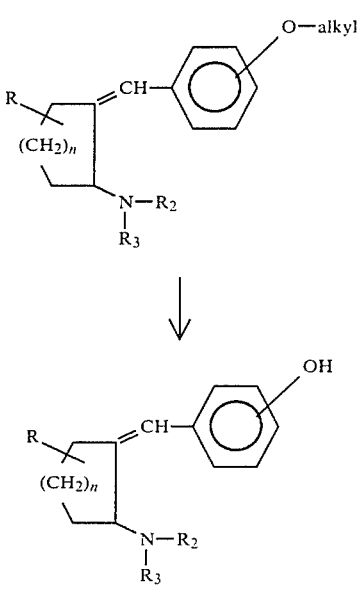
SCHEME IV
PROCESS-AMINE PRODUCTS
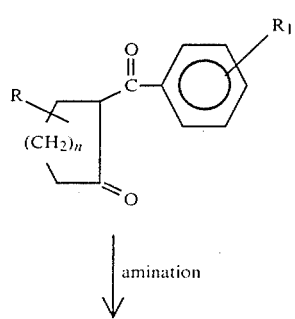
↓ amination
-continued
SCHEME IV
PROCESS-AMINE PRODUCTS
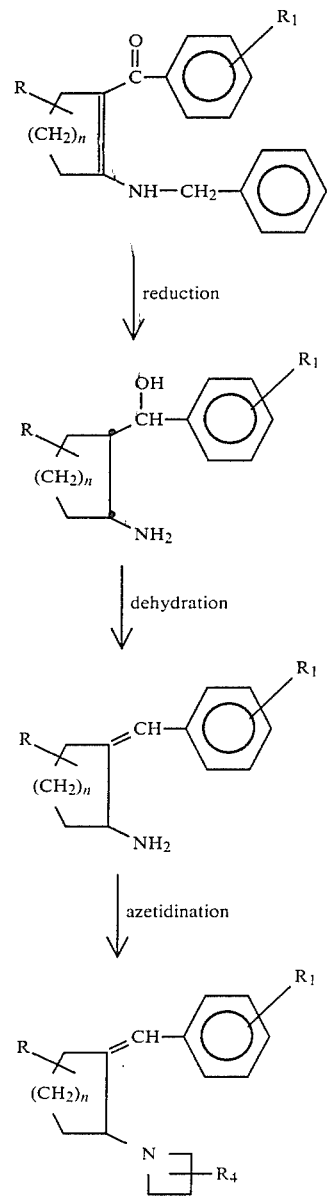
SCHEME V
PROCESS-AMINES VIA CYCLOALKANONE AMINATION
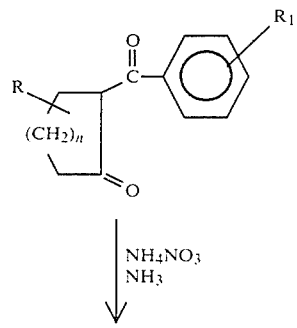
↓ NH₄NO₃
  NH₃

SCHEME V

PROCESS-AMINES VIA CYCLOALKANONE AMINATION

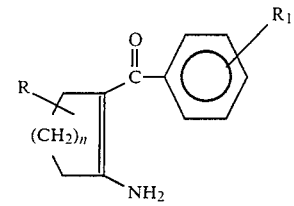

↓ 1. HClO$_4$, THF, NaBH$_3$CN
↓ 2. NaBH$_4$, ethanol

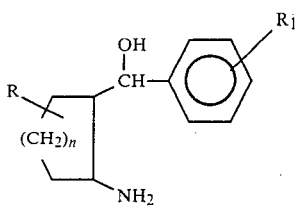

↓ dehydration

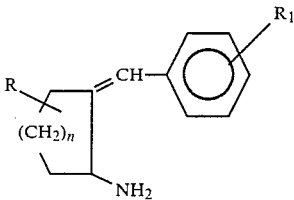

↓ azetidination (optional)

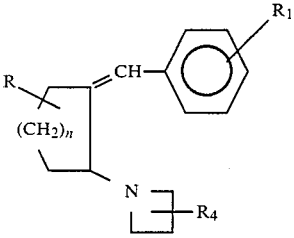

SCHEME VI

PROCESS - FROM 2-PHENYLMETHYLENECYCLOALKANONES

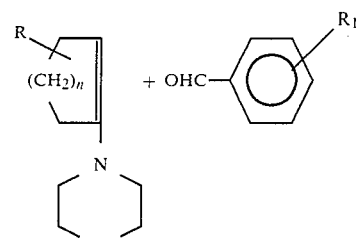

↓ alkylation-dehydration

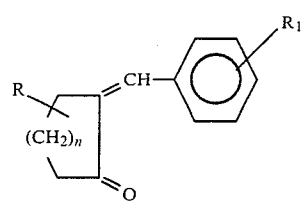

↓ amination

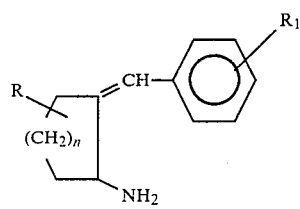

↓ azetidination via 1,3-dibromopropane (optional)

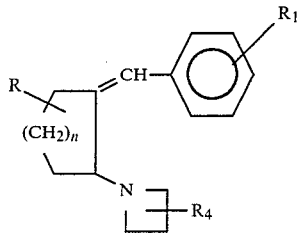

SCHEME VII

PROCESS PREPARATION OF 2-(PHENYLMETHYLENEOCYCLOALKANONES

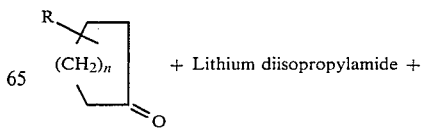 + Lithium diisopropylamide +

-continued
SCHEME VII
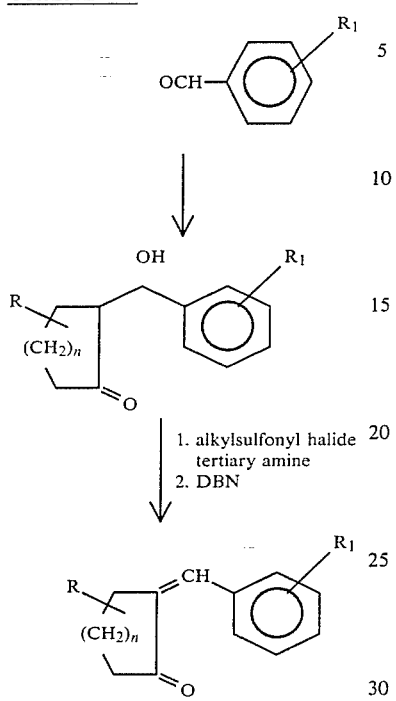
1. alkylsulfonyl halide
   tertiary amine
2. DBN
SCHEME VIII
PROCESS - SYNTHESIS OF Z ISOMER
-continued
SCHEME VIII
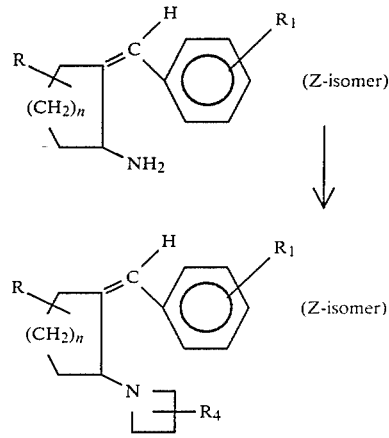
SCHEME IX
PROCESS -
DIRECT AZETIDINATION OF CYCLOALKANONE
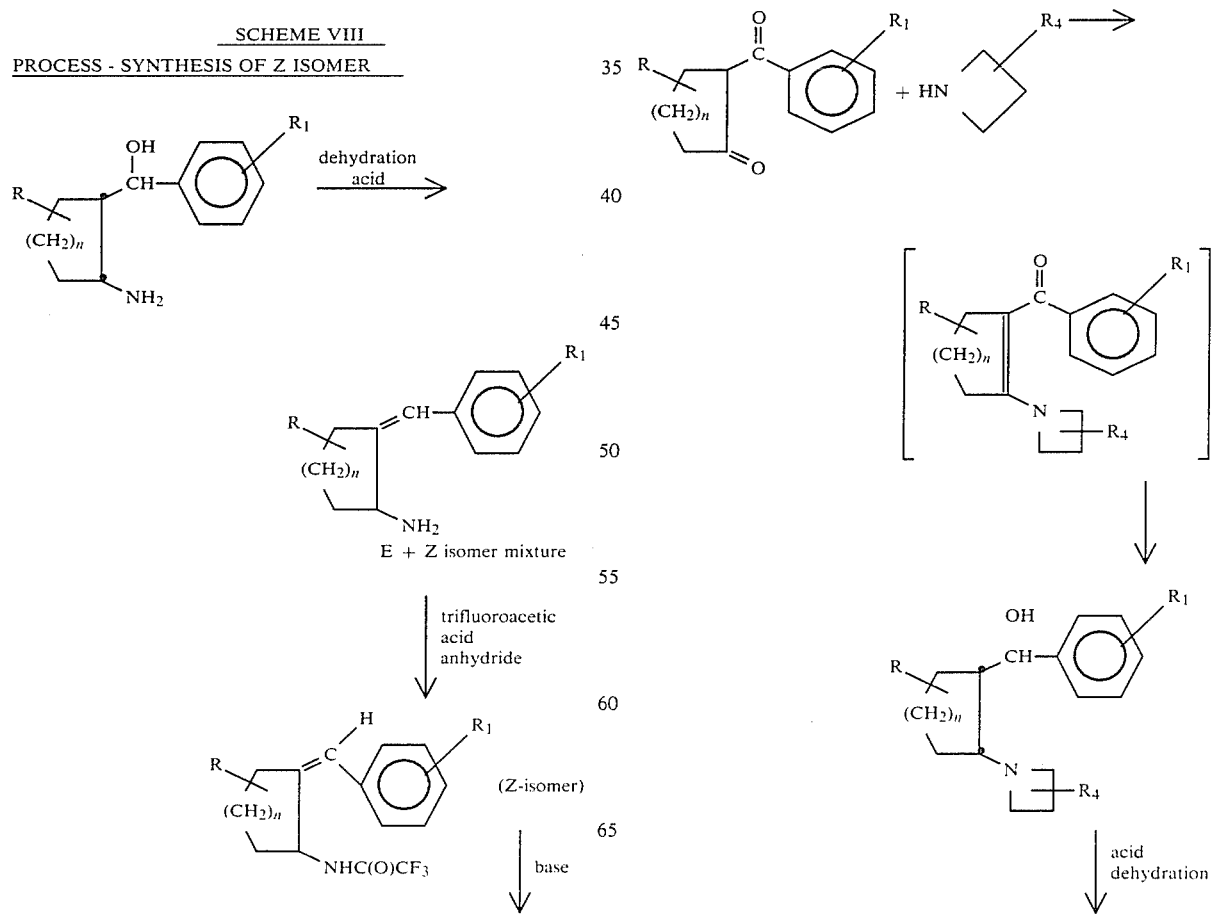

-continued
SCHEME IX

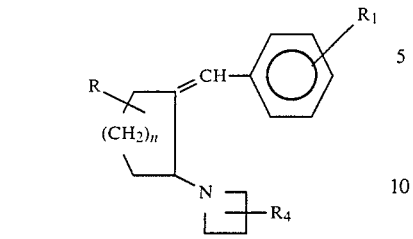

I claim:
1. A compound of the formula

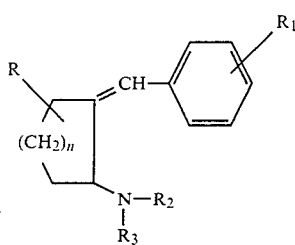

wherein
n is 1, 2, 3 or 4 so that the resulting cycloalkyl ring is cyclopentyl, cyclohexyl, cycloheptyl or cyclooctyl;
R is hydrogen, $C_1$ to $C_3$-alkyl;
$R_1$ represents hydrogen or from one to two substituents on the phenyl ring selected from the group consisting of a halogen having an atomic number of from 9 to 35;
$C_1$ to $C_4$-alkyl,
trifluoromethyl,
hydroxy, carboxyl, and sodium and potassium salts thereof,
$C_1$ to $C_2$-alkyloxy,
($C_1$ to $C_2$-alkyloxy)carbonyl (—C(O)O—$C_1$ to $C_2$-alkyl),
$C_2$ to $C_5$-alkanoyloxy (—OC(O)—$C_1$ to $C_4$-alkyl),
hydroxymethyl,
($C_1$ to $C_2$-alkanoyl)oxymethyl ($C_1$ to $C_2$-alkanoyl-OCH$_2$),
—O—(CH$_2$)$_r$—O— bonded to the 3- and 4-ring carbons, where r is 1 or 2,
($C_1$ to $C_3$-alkyl)oxymethyl ($C_1$ to $C_3$-alkyl-OCH$_2$),
($C_1$ to $C_2$-alkyl)oxycarbonylmethyl, ($C_1$ to $C_2$-alkyl—O—C(O)—CH$_2$—),
—CH(($R_{10}$)—C(O)—OR$_{11}$ wherein $R_{10}$ is hydrogen or $C_1$ to $C_3$-alkyl and $R_{11}$
is hydrogen or $C_1$ to $C_3$-alkyl,
phenyl,
phenoxy,
benzyloxy,
benzoyloxy,
phenyl-$C_1$ to $C_3$-alkyl,
phenylethenyl,
phenoxymethyl,
and such phenyl, phenoxy, benzyloxy, benzoyloxy, phenyl-($C_1$ to $C_3$-alkyl), phenylethenyl, and phenoxymethyl groups substituted on the phenyl ring carbon atoms thereof with one or two substituents selected from the group consisting of halogen as defined above, trifluoromethyl, $C_1$ to $C_2$-alkyl, $C_1$ to $C_2$-alkyl, $C_1$ to $C_2$-alkyloxy, and hydroxy;
$R_2$ and $R_3$ are taken together with the nitrogen to which they are bonded to complete an azetidine ring of the formula

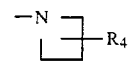

wherein $R_4$ denotes hydrogen, $C_1$ to $C_2$-alkyl, 3-hydroxy, 3-($C_1$ to $C_2$-alkyloxy)- or 3-($C_1$ to $C_2$-alkanoyloxy); and the acid addition salts of such compounds.

2. A compound according to claim 1 wherein the compound is of the formula

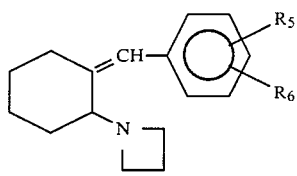

wherein each of
$R_5$ and $R_6$ is selected from the group consisting of
hydrogen,
halogen having an atomic number of from 9 to 35,
$C_1$ to $C_4$-alkyl,
trifluoromethyl,
hydroxy,
carboxyl, and sodium and potassium salts thereof,
$C_1$ to $C_2$-alkyloxy,
($C_1$ to $C_2$-alkyloxy)carbonyl,
$C_2$ to $C_5$-alkanoyloxy,
hydroxymethyl,
($C_1$ to $C_2$-alkanoyl)oxymethyl,
—O—(CH$_2$)$_r$—O— bonded to the 3-and 4-ring carbons where r is 1 or 2,
($C_1$ to $C_2$-alkyloxy)methyl,
($C_1$ to $C_2$-alkyl)oxycarbonylmethyl,
—CH($R_{10}$)—C(O)—OR$_{11}$ wherein $R_{10}$ is hydrogen or $C_1$ to $C_3$-alkyl and
$R_{11}$ is hydrogen or $C_1$ to $C_3$-alkyl,
phenyl,
phenoxy,
benzyloxy,
benzoyloxy,
phenyl-$C_1$ to $C_3$-alkyl,
phenylethenyl, phenoxymethyl and said phenyl ring containing groups substituted on phenyl ring carbons thereof with one or two substituents selected from the group consisting of halogen as defined above, trifluoromethyl, $C_1$ to $C_2$-alkyl, $C_1$ to $C_2$-alkyloxy, and hydroxy;
or a pharmaceutically acceptable salt thereof.

3. A compound according to claim 1 wherein the compound is of the formula

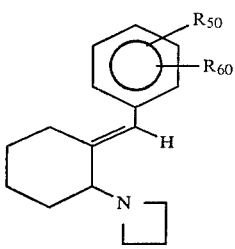

(III)

wherein each of R₅₀ and R₆₀ represents hydrogen or a substituent selected from the group consisting of a halogen having an atomic number of from 9 to 35, $C_1$ to $C_4$-alkyl, trifluoromethyl, hydroxy, $C_1$ to $C_2$-alkyloxy, phenoxy and —CH(R₁₀)—C(O)—OR₁₁ where R₁₀ is hydrogen or $C_1$ to $C_3$-alkyl and R₁₁ is hydrogen or $C_1$ to $C_3$-alkyl; and the pharmacologically acceptable salts thereof.

4. A compound according to claim 1 wherein the compound is a compound of the formula

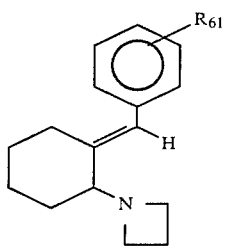

(IV)

wherein R₆₁ represents benzyloxy or benzyloxy substituted on ring carbons thereof by one or two substituents selected from the group consisting of halogen as defined above, trifluoromethyl, $C_1$ to $C_2$-alkyl, $C_1$ to $C_2$-alkyloxy and hydroxy; and the pharmacologically acceptable acid addition salts thereof.

5. A compound according to claim 1 wherein the compound is of the formula

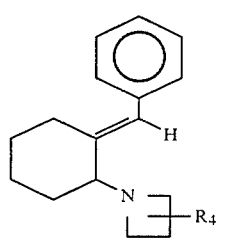

(V)

wherein R₄ represents $C_1$ to $C_2$-alkyl, 3-hydroxy, 3-($C_1$ to $C_2$-alkyloxy) or 3-($C_1$ to $C_2$-alkanoyloxy), and the pharmaceutically acceptable acid addition salts thereof.

6. A compound according to claim 3 wherein the compound is 1-[2-(phenylmethylene)cyclohexyl]azetidine, or an acid addition salt thereof.

7. A compound according to claim 6 wherein the 1-[2-(phenylmethylene)cyclohexyl]azetidine is in a substantially pure E-isomer racemate (±) form, or a pharmacologically acceptable salt thereof.

8. A compound according to claim 2 wherein the compound is 1-[2-(phenylmethylene)cyclohexyl]azetidine which is in a substantially pure Z-isomer racemate form, or a pharmacologically acceptable salt thereof.

9. A compound according to claim 6 wherein the 1-[2-(phenylmethylene)cyclohexyl]azetidine is the substantially pure dextro(+)-E-isomeric form, or a pharmacologically acceptable salt thereof.

10. A compound according to claim 6 wherein the 1-[2-(phenylmethylene)cyclohexyl]azetidine is the substantially pure levo(−)-E-isomeric form, or a pharmacologically acceptable salt thereof.

11. A compound according to claim 6 wherein the compound is 1-[2-(phenylmethylene)cyclohexy]azetidine succinate salt.

12. A compound according to claim 6 wherein the compound is 1-[2-(phenylmethylene)cyclohexyl]azetidine maleate salt.

13. A compound according to claim 2 wherein the compound is 1-[2-[(4-fluorophenyl)methylene]cyclohexyl]azetidine, or a pharmaceutically acceptable salt thereof.

14. A compound according to claim 2 wherein the compound is 1-[2-[(3-fluorophenyl)methylene]cyclohexyl]azetidine, or a pharmaceutically acceptable salt thereof.

15. A compound according to claim 2 wherein the compound is 1-[2-[(4-chlorophenyl)methylene]cyclohexyl]azetidine, or a pharmaceutically acceptable salt thereof.

16. A compound according to claim 2 wherein the compound is 1-[2-[(3,4-dichlorophenyl)methylene]cyclohexyl]azetidine, or a pharmaceutically acceptable salt thereof.

17. A compound according to claim 2 wherein the compound is 1-[2-[(3-fluoro-4-methoxyphenyl)methylene]cyclohexyl]azetidine, or a pharmaceutically acceptable salt thereof.

18. A compound according to claim 2 wherein the compound is 1-[2-[(3,4-difluorophenyl)methylene]cyclohexyl]azetidine, or a pharmaceutically acceptable salt thereof.

19. A compound according to claim 2 wherein the compound is 1-[2-[(3,4-dimethylphenyl)methylene]cyclohexyl]azetidine, or a pharmaceutically acceptable salt thereof.

20. A compound according to claim 2 wherein the compound is 1-[2-[(4-hydroxyphenyl)methylene]cyclohexyl]azetidine, or a pharmaceutically acceptable salt thereof.

21. A compound according to claim 2 wherein the compound is 1-[2-[(4-tert-butylphenyl)methylene]cyclohexyl]azetidine, or a pharmaceutically acceptable salt thereof.

22. A compound according to claim 2 wherein the compound is 1-[2-[(4-acetoxyphenyl)methylene]cyclohexyl]azetidine, or a pharmaceutically acceptable salt thereof.

23. A compound according to claim 2 wherein the compound is 1-[2-[[(3,4-methylenedioxy)phenyl]methylene]cyclohexyl]azetidine, or a pharmaceutically acceptable salt thereof.

24. A compound according to claim 2 wherein the compound is 1-[2-[(4-ethoxycarbonylphenyl)methylene]cyclohexyl]azetidine, or a pharmaceutically acceptable salt thereof.

25. A compound according to claim 2 wherein the compound is 1-[2-[(3-hydroxy-4-methoxyphenyl)methylene]cyclohexyl]azetidine, or a pharmaceutically acceptable salt thereof.

26. A compound according to claim 2 wherein the compound is 1-[2-[(3-methoxy-4-hydroxyphenyl)methylene]cyclohexyl]azetidine, or a pharmaceutically acceptable salt thereof.

27. A compound according to claim 2 wherein the compound is 1-[2-[[(4-phenylcarbonyloxy)phenyl]methylene]cyclohexyl]azetidine, or a pharmaceutically acceptable salt thereof.

28. A compound according to claim 2 wherein the compound is 1-[2-[[4-(2-phenylethyl)phenyl]methylene]cyclohexyl]azetidine, or a pharmaceutically acceptable salt thereof.

29. A compound according to claim 2 wherein the compound is 1-[2-[(4-phenoxyphenyl)methylene]cyclohexyl]azetidine, or a pharmaceutically acceptable salt thereof.

30. A compound according to claim 5 wherein the compound is 2-methyl-1-[2-(phenylmethylene)cyclohexyl]azetidine, or a pharmacologically acceptable salt thereof.

31. A compound according to claim 5 wherein the compound is 3-methyl-1-[2-(phenylmethylene)cyclohexyl]azetidine, or a pharmacologically acceptable salt thereof.

32. A compound according to claim 4 wherein the compound is 1-[2-[[4-(benzyloxy)phenyl]methylene]cyclohexyl]azetidine, or a pharmacologically acceptable salt thereof.

33. A compound according to claim 4 wherein the compound is 1-[2-[[4-(4-methoxybenzyloxy)phenyl]methylene]cyclohexyl]azetidine, or a pharmacologically acceptable salt thereof.

34. A compound according to claim 4 wherein the compound is 1-[2-[[4-(4-chlorobenzyloxy)phenyl]methylene]cyclohexyl]azetidine, or a pharmacologically acceptable salt thereof.

35. A compound according to claim 4 wherein the compound is 1-[2-[[4-(4-methylbenzyloxy)phenyl]methylene]cyclohexyl]azetidine, or a pharmacologically acceptable salt thereof.

36. A compound according to claim 4 wherein the compound is 1-[2-[[4-(3,4-dichlorobenzyloxy)phenyl]methylene]cyclohexyl]azetidine, or a pharmacologically acceptable salt thereof.

37. A compound according to claim 4 wherein the compound is 1-[2-[[4-[4-(trifluoromethyl)benzyloxy]phenyl]methylene]cyclohexyl]azetidine, or a pharmacologically acceptable salt thereof.

38. A compound according to claim 1 wherein the compound is of the formula

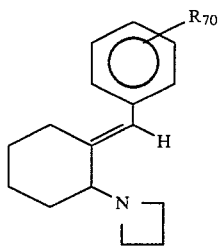 (VI)

wherein $R_{70}$ is selected from the group consisting of hydroxymethyl, $C_1$ to $C_4$-alkyloxymethyl, phenoxymethyl, carboxyl, sodium and potassium salts of carboxyl, $C_1$ to $C_3$-alkyloxycarbonyl, $C_2$ to $C_5$-alkanoyloxy, and benzyloxy groups, and the pharmacologically acceptable acid addition salts thereof.

39. A compound according to claim 38 wherein the compound is 1-[2-[[4-(hydroxymethyl)phenyl]methylene]cyclohexyl]azetidine, or a pharmacologically acceptable salt thereof.

40. A compound according to claim 38 wherein the compound is 1-[2-[[4-(phenylcarbonyloxy)phenyl]methylene]cyclohexyl]azetidine, or a pharmacologically acceptable salt thereof.

41. A compound according to claim 38 wherein the compound is 1-[2-[[4-(tert-butylcarbonyloxy)phenyl]methylene]cyclohexyl]azetidine, or a pharmacologically acceptable salt thereof.

42. A composition useful in pharmaceutically effective dosage unit forms for alleviating pain and/or depression in warm-blooded animals which comprises a compound of claim 1 in combination with a pharmaceutically acceptable carrier.

43. A composition according to claim 42 wherein the compound of claim 1 is a compound according to claim 2.

44. A composition according to claim 43 wherein the compound of claim 2 is 1-[2-(phenylmethylene)cyclohexyl]azetidine or a pharmaceutically acceptable salt thereof.

45. A composition according to claim 44 useful in pharmaceutically effective dosage unit forms for alleviating pain and/or depression in warm-blooded animals wherein the active compound is in a substantially pure E-isomer racemate (E)-($\pm$)-1-[2-(phenylmethylene)cycloheyl]azetidine or a pharmaceutically acceptable salt thereof.

46. A composition according to claim 45 wherein the compound is (E)-($\pm$)-1-[2-(phenylmethylene)cyclohexyl]azetidine succinate salt.

47. A method for alleviating pain and/or depression which comprises administering to an animal suffering pain and/or depression an effective amount of a compound according to claim 1 in a pharmaceutical dosage unit form.

48. A method according to claim 47 wherein the effective dosage amount of the compound of claim 1 ranges between 0.5 and 350 mg of the claim 1 compound per dose.

49. A method according to claim 48 wherein the active claim 1 compound is 1-[2-(phenylmethylene)cyclohexyl]azetidine, or a pharmaceutically acceptable acid addition salt thereof.

50. A method according to claim 49 for alleviating pain and depression which comprises administering to an animal suffering pain and depression an effective amount of the (E)-isomer racemate ($\pm$) form of the active compound, namely, (E)-($\pm$)-1-[2-(phenylmethylene)cyclohexyl]-azetidine or a pharmaceutically acceptable salt thereof.

51. A method according to claim 50 wherein the compound is (E)-($\pm$)-1-[2-(phenylmethylene)cyclohexyl]azetidine succinate salt.

* * * * *